(12) United States Patent
Rathbun et al.

(10) Patent No.: US 9,468,467 B2
(45) Date of Patent: Oct. 18, 2016

(54) BONE SUPPORT APPARATUS

(71) Applicant: DEPUY SYNTHES PRODUCTS, LLC, Raynham, MA (US)

(72) Inventors: David Rathbun, West Chester, PA (US); Roberto Khatchadourian, West Chester, PA (US); Scott Jacobs, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 241 days.

(21) Appl. No.: 13/757,267

(22) Filed: Feb. 1, 2013

(65) Prior Publication Data
US 2014/0222074 A1 Aug. 7, 2014

(51) Int. Cl.
*A61B 17/70* (2006.01)
*A61B 17/86* (2006.01)

(52) U.S. Cl.
CPC ....... *A61B 17/7014* (2013.01); *A61B 17/7004* (2013.01); *A61B 17/705* (2013.01); *A61B 17/707* (2013.01); *A61B 17/7031* (2013.01); *A61B 17/8695* (2013.01)

(58) Field of Classification Search
CPC .......... A61B 17/7014; A61B 17/7004; A61B 17/7031; A61B 17/7049; A61B 17/705; A61B 17/707; A61B 17/8695
USPC ....... 606/258, 246, 254, 255, 257, 259, 260, 606/261, 276, 277, 279, 105
See application file for complete search history.

(56) References Cited

U.S. PATENT DOCUMENTS

| | | | |
|---|---|---|---|
| 4,800,874 A | | 1/1989 | David et al. |
| 5,030,235 A | | 7/1991 | Campbell, Jr. |
| 5,092,889 A | * | 3/1992 | Campbell, Jr. ............ 623/23.47 |
| 5,261,908 A | * | 11/1993 | Campbell, Jr. ............... 606/279 |
| 5,330,472 A | * | 7/1994 | Metz-Stavenhagen ......... 606/53 |
| 5,593,407 A | | 1/1997 | Reis |
| 5,632,744 A | | 5/1997 | Campbell, Jr. |
| 5,800,434 A | | 9/1998 | Campbell, Jr. |
| 7,850,719 B2 | | 12/2010 | Gournay et al. |
| 7,850,732 B2 | | 12/2010 | Heinz |
| 2005/0267475 A1 | * | 12/2005 | Miller, III ....................... 606/69 |
| 2008/0021456 A1 | | 1/2008 | Gupta et al. |
| 2010/0137913 A1 | | 6/2010 | Khatchadourian et al. |

OTHER PUBLICATIONS

*Vertical Expandable Prosthetic Titanium Rib*, Technique Guide, Synthes Spine, pp. 1-2.
Vertical Expandable Prosthetic Titanium Rib II, Technique Guide, *Synthes Spine*, pp. 1-12.

* cited by examiner

*Primary Examiner* — Pedro Philogene
*Assistant Examiner* — David C Comstock
(74) *Attorney, Agent, or Firm* — Dunlap Codding, P.C.

(57) ABSTRACT

A bone support apparatus includes a first bone connector with a first bone cradle insert configured to contact a patient's bone and constructed of a resilient material, a second bone connector configured to contact a patient's bone, and an adjustable rod assembly having a first end connected to the first bone connector and a second end connected to the second bone connector. The adjustable rod assembly has a first elongated member, a second elongated member, and an expansion member with a first end adjustably connected to the first elongated member and a second end adjustably connected to the second elongated member. The distance between the first bone connector and the second bone connector is adjustable by moving at least one of the first end and the second end relative to the first and second elongated member.

7 Claims, 17 Drawing Sheets

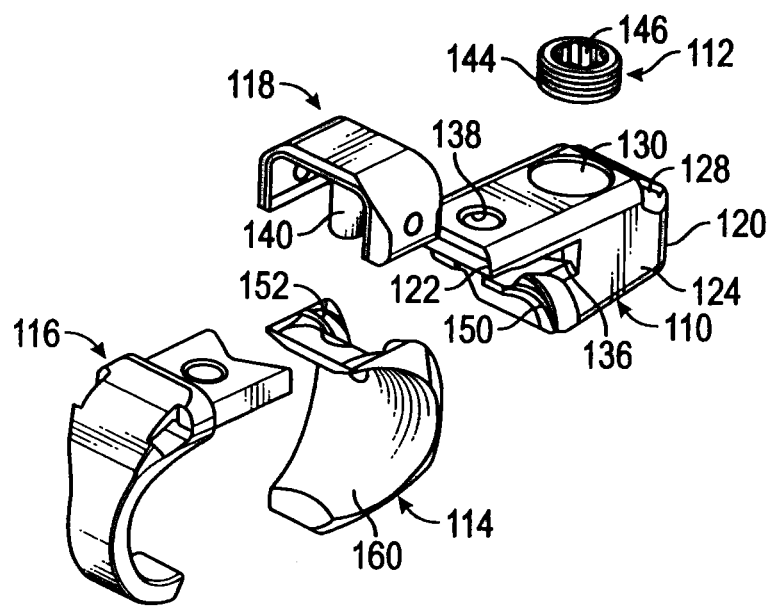
FIG. 2
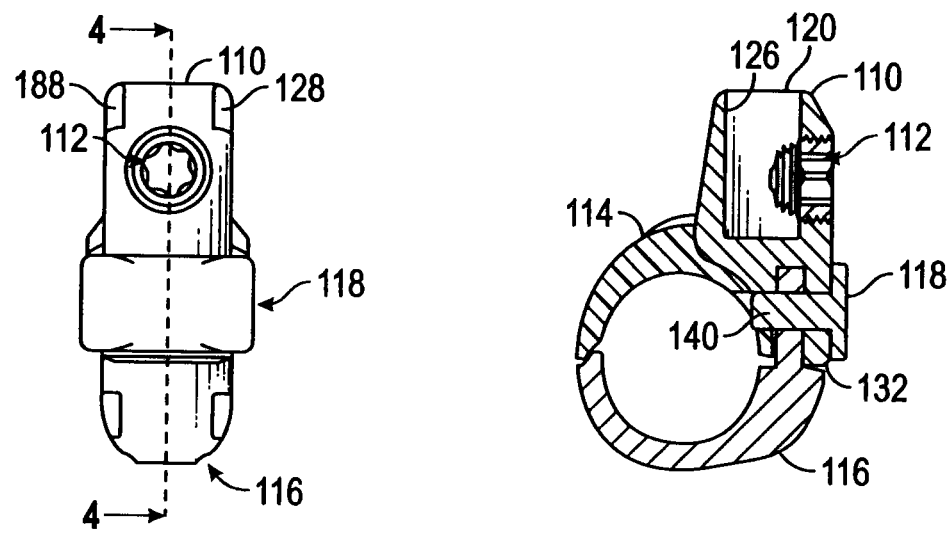
FIG. 3
FIG. 4

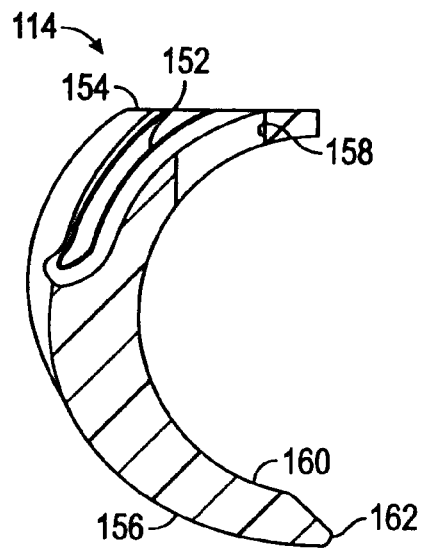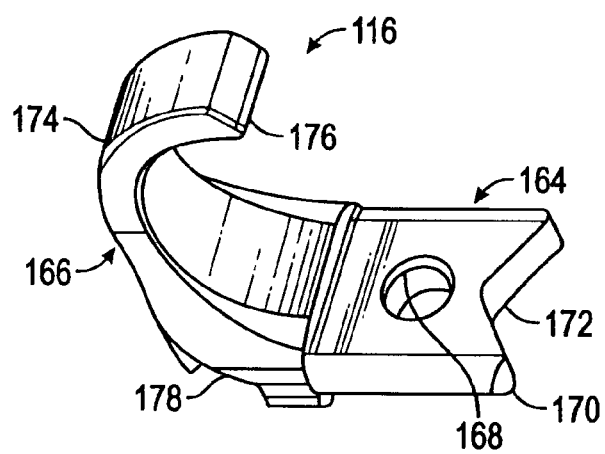
FIG. 8  FIG. 9
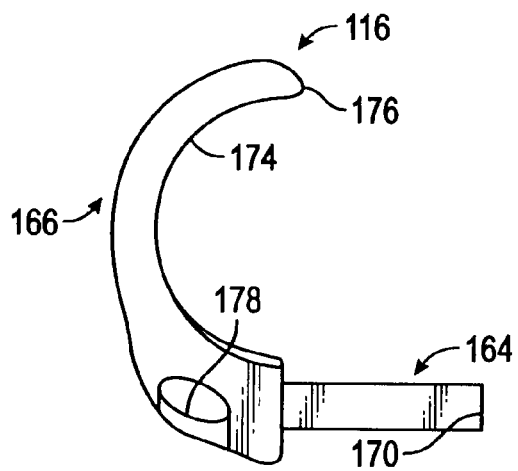
FIG. 10

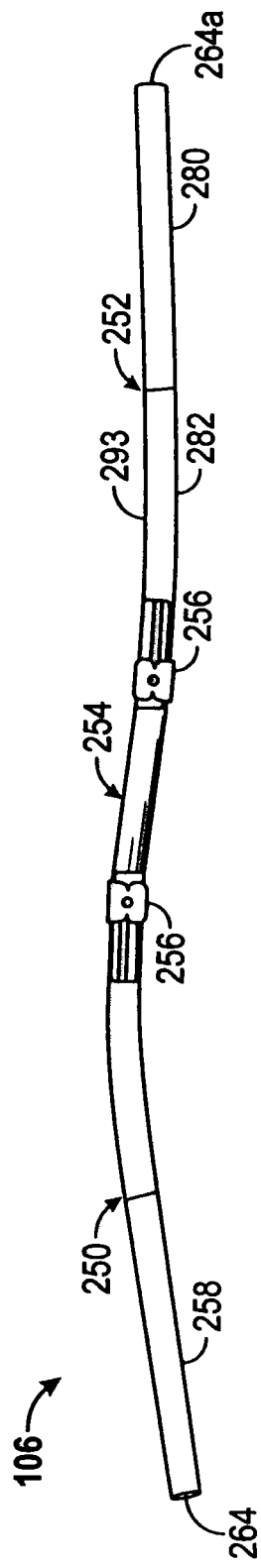
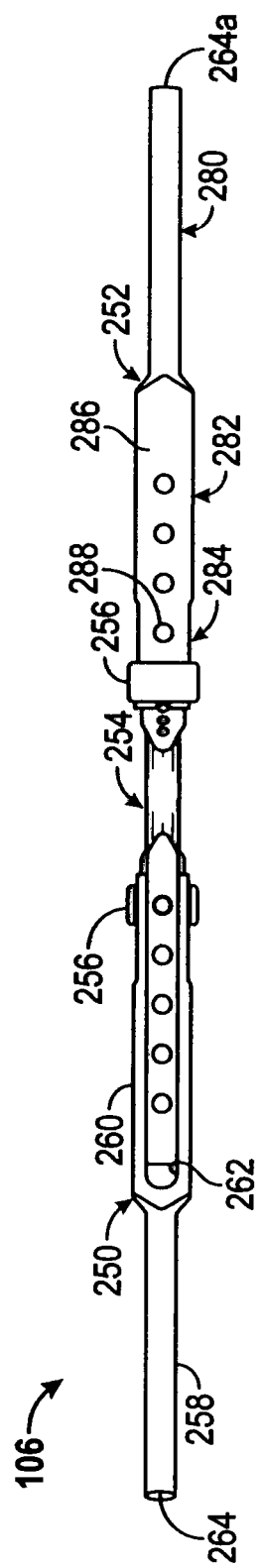

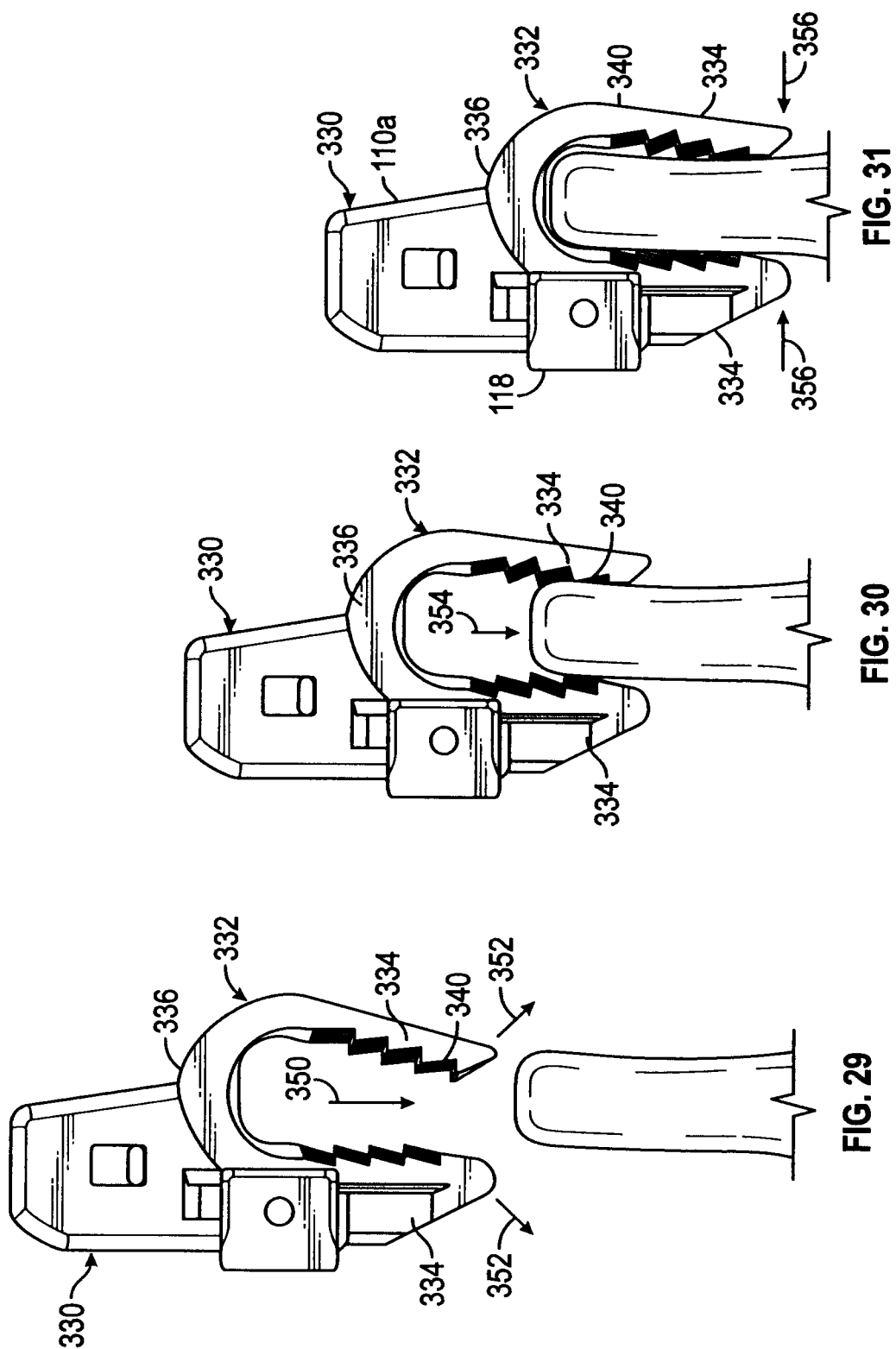

BONE SUPPORT APPARATUS

BACKGROUND

1. Field of the Inventive Concepts

The inventive concepts disclosed herein generally relate to surgically implantable devices, and more particularly, but not by way of limitation, to a bone support apparatus and to methods of using same.

2. Brief Description of Related Art

Expandable prosthetic rib (EPR) devices are designed to mechanically stabilize the thorax of a patient to correct three-dimensional thoracic deformities, and to provide improvements in volume for respirations and lung growth in infantile and juvenile patients diagnosed with thoracic insufficiency syndrome. Once the initial implantation procedure is complete and an EPR device is implanted into a patient's body, the EPR device may allow for some adjustability, such as expansion, anatomic distraction, and replacement of some components of the EPR device through subsequent surgical procedures, which are generally less invasive than the initial implantation procedure. Available EPR devices are typically elongated devices that are attached to one or more of the patient's ribs and to the patient's pelvis, such that the EPR device extends along the spine of the patient.

EPR devices are typically attached to the patient's rib via a multi-part enclosed cradle, which extends from the posterior side towards the anterior side of the patient. The cradle typically substantially encloses the patient's rib to prevent the EPR device from becoming displaced during breathing or other movements of the patient.

Available EPR devices allow for limited expansion in an area superior to the thoracic-lumbar junction, and generally are replaced with a larger EPR device once the limited adjustability is exceeded by the patient's growth. Available expandable sections have a kyphosis radius, which may tend to push the patient's upper thoracic forward and may inadvertently contribute to increased kyphosis in some patients. Further, since the expandable sections of available EPR devices are typically limited to the thoracic region, the amount of expansion available is limited compared to the length of the total implantable EPR device, before major surgical revisions (e.g., implanting a larger EPR device) are needed as the patient's body grows. Available EPR devices are also typically made of rigid materials, and do not allow for flexing or absorbing shocks and movements of the patient's trunk or spine during normal activities carried out by the patient.

Finally, some available EPR devices have an end that is typically attached to the patient's pelvis via a S-shaped hook, which S-shaped hook may generally extend from the posterior side of the patient to the anterior side of the patient. Available S-shaped hooks typically rest on top of the iliac crest of the patient, and due to their S-shape, tend to inherently have a limited contact area with the iliac crest.

SUMMARY

In one aspect, the inventive concepts disclosed herein are directed to a bone support apparatus, comprising a first bone connector having a first bone cradle insert configured to contact a patient's bone and constructed of a resilient material, a second bone connector configured to contact a patient's bone, and an adjustable rod assembly having a first end connected to the first bone connector and a second end connected to the second bone connector, the adjustable rod assembly configured to adjust a distance between the first end and the second end.

In another aspect, the inventive concepts disclosed herein are directed to a bone support kit, comprising a first bone connector having a first bone cradle insert configured to contact a patient's bone and constructed of a resilient material, a second bone connector configured to contact a patient's bone, and an adjustable rod assembly having a first end connectable to the first bone connector and a second end connectable to the second bone connector, the adjustable rod assembly configured to adjust a distance between the first end and the second end.

In yet another aspect, the inventive concepts disclosed herein are directed to a bone support apparatus, comprising a first bone connector configured to contact a patient's bone, a second bone connector configured to contact a patient's bone, and an adjustable rod assembly. The adjustable rod assembly comprises a first elongated member connected to the first bone connector, a second elongated member connected to the second bone connector, and an expansion member having a first end adjustably connected to the first elongated member and a second end adjustably connected to the second elongated member, such that a distance between the first bone connector and the second bone connector is adjustable by moving at least one of the first end of the expansion member relative to the first elongated member and the second end of the expansion member relative to the second elongated member.

In a further aspect, the inventive concepts disclosed herein are directed to a bone support kit, comprising a first bone connector configured to contact a patient's bone, a second bone connector configured to contact a patient's bone, and an adjustable rod assembly connectable to the first bone connector and the second bone connector. The adjustable rod assembly comprises a first elongated member configured to connect to the first bone connector, a second elongated member configured to connect to the second bone connector, and an expansion member having a first end configured to adjustably connect to the first elongated member and a second end configured to adjustably connect to the second elongated member, such that a distance between the first bone connector and the second bone connector is adjustable by moving at least one of the first end of the expansion member relative to the first elongated member and the second end of the expansion member relative to the second elongated member.

BRIEF DESCRIPTION OF THE DRAWINGS

Like reference numerals in the figures may represent and refer to the same or similar element or function. Implementations of the inventive concepts disclosed herein may be better understood when consideration is given to the following detailed description thereof. Such description makes reference to the annexed pictorial illustrations, schematics, graphs, drawings, and appendices. In the drawings:

FIG. 2 is an exploded perspective view of an exemplary embodiment of a rib connector of the bone support apparatus of FIG. 1.

FIG. 3 is a top plan view of the rib connector of FIG. 2.

FIG. 4 is a cross-sectional view along line 4-4 of FIG. 3.

FIG. 8 is a cross-sectional view along line 8-8 of FIG. 7.

FIG. 9 is a perspective view of a cradle end half.

FIG. 10 is a side view of the cradle end half of FIG. 9.

FIG. 22 is a side view of an adjustable rod.

FIG. 23 is a top plan view of the adjustable rod assembly of FIG. 22.

FIG. 29 is a diagrammatic view of the ilium connector of FIG. 27 being attached to an ilium.

FIG. 30 is a diagrammatic view of the ilium connector of FIG. 27 shown partially attached to the ilium.

FIG. 31 is a diagrammatic view of the ilium connector of FIG. 27 shown attached to the ilium.

DETAILED DESCRIPTION OF EXEMPLARY EMBODIMENTS

Figure 1:
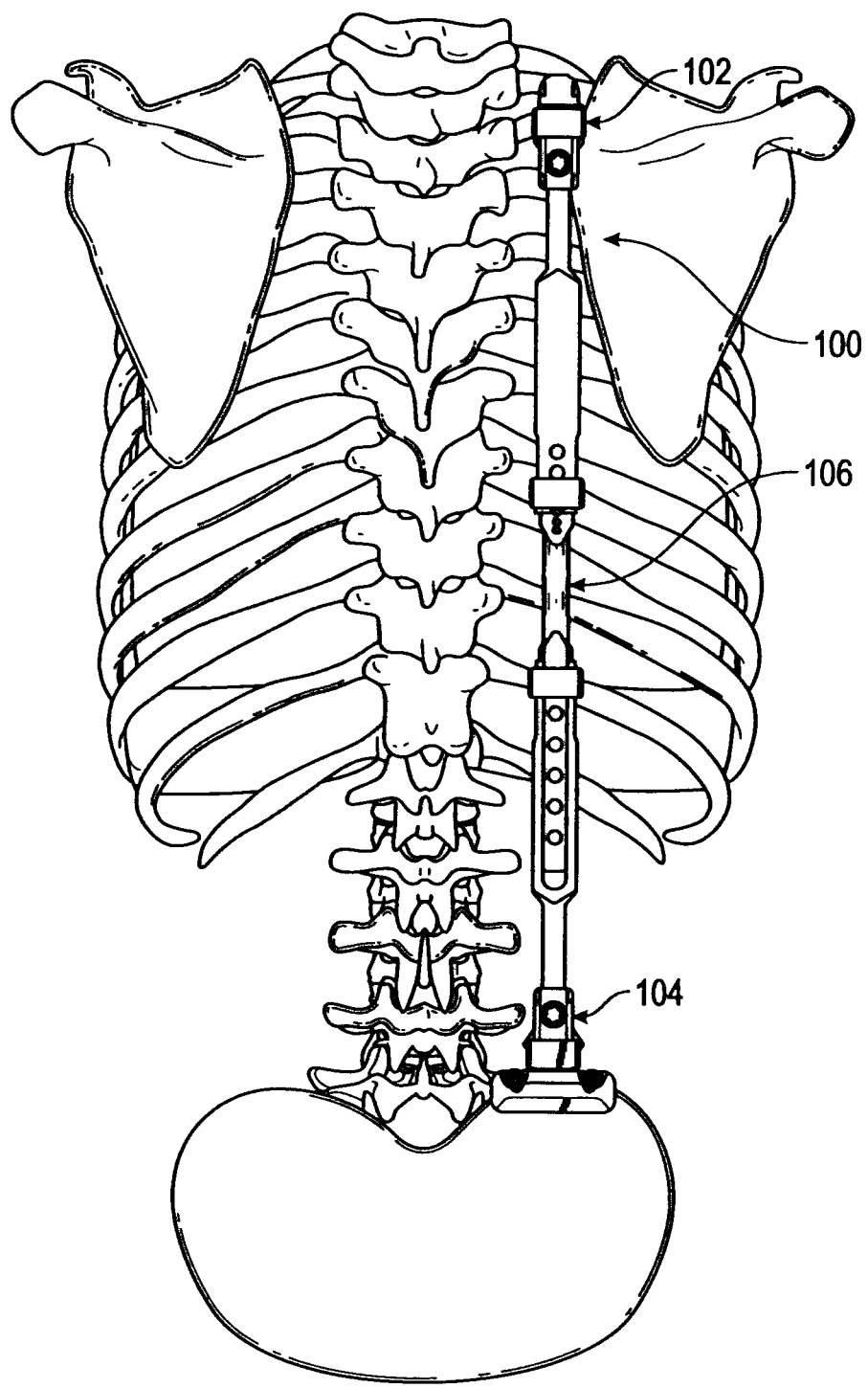
FIG. 1 is a perspective view of a bone support apparatus constructed in accordance with the inventive concepts disclosed herein shown attached to a patient's rib and ilium.
Figure 5:
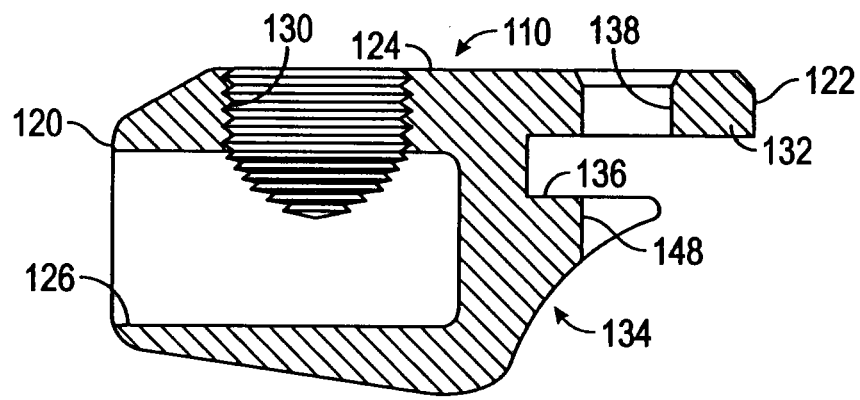
FIG. 5 is a cross-sectional view of a base member of the rib connector.
Figure 6:
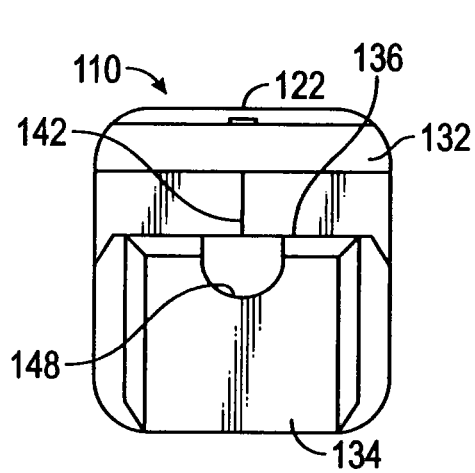
FIG. 6 is an end view of the base member.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description only and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

As used herein the notation "a-n" appended to a reference numeral is intended as merely convenient shorthand to reference one, or more than one, and up to infinity, of the element or feature identified by the respective reference numeral (e.g., 134a-n). Similarly, a letter following a reference numeral is intended to reference an embodiment of the feature or element that may be similar, but not necessarily identical, to a previously described element or feature bearing the same reference numeral (e.g., 148, 148a, 148b, etc.). Such shorthand notations are used for purposes of clarity and convenience only, and should not be construed to limit the instant inventive concept(s) in any way, unless expressly stated to the contrary.

Further, unless expressly stated to the contrary, "or" refers to an inclusive "or" and not to an exclusive "or." For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

As is known by persons of ordinary skill in the art, established human anatomical orientation designations are used to avoid ambiguities when referring to a body part relative to another body part. A standard anatomical position (i.e., standing upright facing forward with arms to the side, palms facing forward, thumbs pointing laterally away from the body) has been established, and such orientation designations refer to the various body parts in the standard position, without regard to their actual position. For the purposes of the instant disclosure such standard human anatomy terminology may be used to describe the various orientation and interrelationships of the different parts of a user's body. For example, the terms "anterior," "posterior," "superior," "inferior," "lateral," "medial," and related terms or phrases designate relative positions and orientations in the patient's body to which reference is made and are not meant to be limiting. Further, the terms "left," "right," "lower,' "upper," "top," and "bottom" may designate general directions in the drawings to which reference is made, for example, and are not meant to be limiting. The terms "inner," "inwardly," or "distally," and "outer," "outwardly," or "proximally" may refer to directions toward or away from the geometric center of the device and related parts thereof, or the patient's body, for example, and are not intended to be limiting.

As used herein, the term "patient" is not limited to a human being, and is intended to include all organisms, whether alive or dead, including any species having soft tissues and bones. For example, a device and a method according to the instant disclosure may be used in a living human, horse, cow, sheep, cat, dog, and the like. In another example, a device or a method according to the instant disclosure may be used in a non-living organism or in an artificial anatomical model to train medical or veterinary personnel in surgical techniques. Further, a virtual representation of a device or of a method according to the instant disclosure may be used in a virtual simulation to train medical or veterinary personnel in surgical techniques, for example.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Referring now to the drawings and more particularly to FIG. 1, an exemplary embodiment of a bone support apparatus 100 according to the inventive concepts disclosed herein is shown attached to a patient's body. The bone support apparatus 100 may function as an EPR device and may include a rib connector 102, an ilium connector 104, and an adjustable rod assembly 106 connected to the rib connector 102 and to the ilium connector 104. In some embodiments of the inventive concepts disclosed herein, the bone support apparatus 100 may include modular components that may be interchangeable with one another in the same bone support apparatus 100, or between a first bone support apparatus 100 and a second bone support apparatus 100, as will be described in detail below. For example, one or more modular components may be interchangeable with one another, such as by being interchangeable between the rib connector 102, the ilium connector 104, and the adjustable rod assembly 106, as will be described herein below.

The bone support apparatus 100 may be implemented as any suitable surgically implantable device, as will be described herein below. In some exemplary embodiments of the inventive concepts disclosed herein the bone support apparatus 100 may be configured to mechanically stabilize and distract a patient's thorax to correct three-dimensional thoracic deformities and to provide improvement in volume for respiration and lung growth in the infantile and juvenile patients diagnosed with thoracic insufficiency syndrome. Once the bone support apparatus 100 is implanted in place, its design may allow for expansion, anatomic distraction, and replacement of components thought less-invasive subsequent surgical procedures, for example. A similar bone support apparatus is disclosed in US Publication No. 2010/0137913, the entire disclosure of which is hereby expressly incorporated herein by reference as if expressly set forth herein.

Referring now to FIGS. 2-6, an exemplary embodiment of the rib connector 102 may include a base member 110, a set screw 112, a rib cradle insert 114, a cradle end half 116, and a lock 118.

The base member 110 may be an elongated body having a first end 120, a second end 122, and a side 124 extending between the first end 120 and the second end 122.

The first end 120 may have a substantially cylindrical opening 126 formed therein, the opening 126 may be configured to selectively receive and retain a portion of the adjustable rod assembly 106 therein, as will be described herein below. It is to be understood that the opening 126 may be threaded in some exemplary embodiments.

Further, while the opening 126 is shown as being substantially cylindrical in shape, in some exemplary embodiments the opening 126 may have any desired shape, such as oval, polygonal, star shaped, triangular, rectangular, square, and combinations thereof, for example. As will be appreciated by persons of ordinary skill in the art, the opening 126 may allow for the rotation of the base member 110 about a longitudinal axis of the portion of the adjustable rod assembly 106 when the portion of the adjustable rod assembly 106 is inserted therein. The set screw 112 may be operated to prevent the rotation of the base member 110 about the portion of the adjustable rod assembly 106, or to lock the base member 110 about the portion of the adjustable rod assembly 106 in any desirable position or at any desired angle relative to one another, for example, to adjust the rib connector 102 to varying patient anatomies.

The first end 120 may further include one or more grasping notches 128 formed therein, the one or more grasping notches 128 configured to allow for a surgical tool (not shown) having corresponding protrusions (not shown) to securely grasp the base member 110 during implantation, removal, or adjustment of the base member 110, for example. It is to be understood that in some exemplary embodiments of the inventive concepts the one or more grasping notches 128 may be omitted, while in other exemplary embodiments any number of grasping notches 128 may be used, including a single grasping notch 128, two grasping notches 128, and more than two grasping notches 128, for example.

The side 124 may include a threaded opening 130 that may intersect with the opening 126. The threaded opening 130 may be configured to threadingly receive the set screw 112 therein, such that at least a portion of the set screw 112 may be advanced into the opening 126 by rotating the set screw 112 into the threaded opening 130, for example. The threaded opening 130 and the set screw 112 may have interacting threads configured to allow the set screw 112 to be coupled to the threaded opening 130, for example. It is to be understood that while a single threaded opening 130 is shown in FIGS. 2-6, exemplary embodiments of the inventive concepts disclosed herein may include two, or more than two, threaded openings 130. Further, in some exemplary embodiments, the threads may be omitted from the threaded opening 130 and an external locking element (not shown) may be implemented. As will be appreciated by persons of ordinary skill in the art, while the threaded opening 130 is shown as intersecting the opening 126 at about 90°, some embodiments of the inventive concepts may be implemented with the threaded opening 130 intersecting the opening 126 at any desired angle varying from about 0° to about 180°, for example.

The second end 122 may include a protrusion 132 and a cradle receiver 134 positioned below the protrusion 132 and separated a distance therefrom. The cradle receiver 134 and the protrusion 132 may cooperate to define a slot 136 configured to receive a portion of the cradle end half 116 therein, for example. It is to be understood that while the protrusion 132 and the cradle receiver 134 are shown as extending substantially parallel to one another, in some exemplary embodiments the protrusion 132 and the cradle receiver 134 may be angled relative to one another, such as from about 0° to about 90°.

The protrusion 132 may further include an opening 138 extending therethrough. The opening 138 is configured to receive a pin 140 (FIG. 2) of the lock 118 therein, as will be described herein below in detail. The opening 138 may be formed into the protrusion 132 in any suitable manner, and may have any desired shape, such as substantially circular, oval, square, star-shaped, hexagonal, polygonal, triangular, and combinations thereof, for example. Further, while the opening 138 is shown as extending substantially perpendicularly through the protrusion 132, in some exemplary embodiments the opening 138 may be angled relative to the protrusion 132 at an angle varying from about 0° to about 90°.

The slot 136 may intersect the opening 138, such that the lock 118 may be used to secure the cradle end half 116 into the slot 136, as shown in FIG. 4, for example. The slot 136 may open at the second end 122 and may include in a substantially V-shaped crest 142 (FIG. 6), for example.

The base member 110 may be configured such that a portion of the adjustable rod assembly 106 may be received therein and secured in place via the set screw 112. The rib cradle insert 114 and the cradle end half 116 may be configured to attach to the base member 110 and to substantially enclose and cradle a rib therein. The lock 118 may secure the attachment between the rib cradle insert 114, the cradle end half 116, and the base member 110, for example. The rib connector 102 may be surgically implanted into a patient's body, such that the rib cradle insert 114 and the cradle end half 116 are positioned substantially around one or more of the patient's rib or ribs, for example.

The set screw 112 may include a threaded body 144 having a star drive interface 146 that may function to set the adjustable rod assembly 106 in the base member 110 when the adjustable rod assembly 106 is placed inside the base member 110. The threaded body 144 with star drive interface 146 may function such that when an adjustable rod assembly 106 is placed into the opening 126 of the base member 110, the set screw 112 may be rotated and advanced into the threaded opening 130, and at least partially into the opening 126, to hold the adjustable rod assembly 106 to the base member 110. The set screw 112 may provide transverse compression on the adjustable rod assembly 106 to prevent adjustable rod assembly 106 pull out, and to limit the rotation of the base member 110 and the adjustable rod assembly 106 relative to one another, for example. The set screw 112 may be constructed of any suitable material, such as metals, alloys, surgical steel, titanium, polymers, plastics, resins, and combinations thereof, for example. It is to be understood that in some exemplary embodiments any desired drive interface may be substituted for the star drive interface 146, such as a Phillips drive interface, a hexagonal drive interface, a flat drive interface, and combinations thereof, for example.

The cradle receiver 134 may include a substantially cylindrical notch 148 formed therein, the notch 148 configured to receive the pin 140 (FIG. 2) of the lock 118 as shown in FIG. 4. The cradle receiver 134 may further include a male radial track 150 configured to be matingly received inside a corresponding female radial track 152 formed in the rib cradle insert 114, such that the rib cradle insert 114 may be attached to the cradle receiver 134 adjacent to the slot 136, for example.

The base member 110 may be constructed of any suitable bioinert or bioabsorbable material, such as titanium, surgical steel, plastics, polymeric materials, resins, carbon fiber, polyether ether ketone (PEEK), thermoplastics, metals, and combinations thereof, for example. The base member 110 may be implemented as a multi-purpose base member 110 which connects the rib connector 102 to the adjustable rod assembly 106 as will be described below. The base member 110 may be the base component that other the modular components and the adjustable rod assembly 106 of the bone support apparatus 100 may attach as will be described herein.

Figure 7:
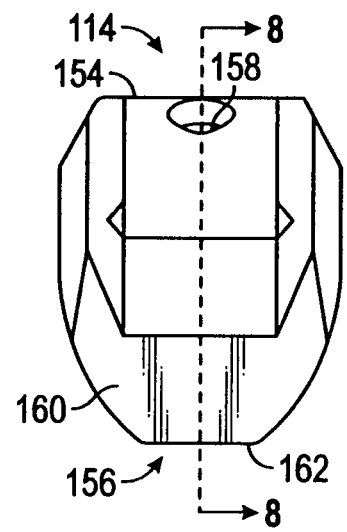
FIG. 7 is an end view of a rib cradle insert of the rib connector.

Referring now to FIGS. 7-8, the rib cradle insert 114 may be implemented as a hook-like structure which may include an attachment end 154 and a cradle 156. The attachment end 154 may include and opening 158 and a female radial track 152. The opening 158 may be configured to correspond to the opening 138 and to align with the opening 138 when the rib cradle insert 114 is attached to the base member 110 to receive the pin 140 of the lock 118 therethrough as shown in FIG. 4, for example.

The female radial track 152 may be configured to correspond to, and to matingly interlock with, the male radial track 150 of the base member 110, such that the rib cradle insert 114 may be selectively radially interfaced with, or otherwise attached to the cradle receiver 134 of the base member 110 by matingly inserting the male radial track 150 into the female radial track 152, for example. When the rib cradle insert 114 is attached to the base member 110, a portion of the attachment end 154 may cooperate with the cradle receiver 134 and with the protrusion 132 to define the slot 136, for example. It is to be understood that in some exemplary embodiments of the inventive concepts disclosed herein, the cradle receiver 134 may have a female radial track (not shown), and the rib cradle insert 114 may have a male radial track (not shown), while in other exemplary embodiments the rib cradle insert 114 may be attached to the cradle receiver 134 in any suitable manner, such as via interlocking features, bolts, screws, rivets, adhesives, and combinations thereof, for example.

The cradle 156 may be arcuate in shape and may have a rib contact surface 160 and an end 162. The rib contact surface 160 is desirably constructed of a resilient plastic material having a tensile modulus or a hardness substantially similar to the typical hardness of human cortical bone, such as PEEK, for example. The material from which the cradle 156 is constructed may include any biocompatible implantable material that has mechanical properties (e.g., hardness, resiliency, or Young's modulus) substantially similar to the mechanical properties of human bone. For example, human cortical bone may generally have a Young's (or tensile) modulus of 14 gigapascals (GPa), and the material selected for the construction of the cradle 156 may have a Young's (or tensile) modulus varying from about 4 to about 24 GPa, from about 10 to about 20 GPa, from about 12 GPa to about 16 GPa, from about 13 GPA to about 15 GPa, or substantially equal to 14 GPa, and combinations thereof, for example.

The rib contact surface 160 may have any desired shape and may taper from the attachment end 154 towards the end 162, for example. The rib contact surface 160 may be implemented to maximize to contact surface between the cradle 156 and a patient's rib. The broad contact interface of the rib contact surface 160 and a patient's rib may reduce migration issues found in some prior art devices. In some exemplary embodiments of the inventive concepts disclosed herein, the rib contact surface 160 may include one or more contact-enhancing or grip-enhancing features (not shown), such as grooves, bumps, knurls, striations, spikes, channels, ridges, and combinations thereof, to prevent or minimize lateral migration of the cradle 156 along the patient's rib and minimize the possibility of migration of the cradle 156 into the patient's rib, for example. Multiple configurations may be implemented for the rib contact surface 160 of the cradle 156 to accommodate different anatomical features found on the rib cage of a patient, for example. The cradle 156 may be implemented in a variety of sizes, shapes, curvature, and angular orientations to match patient anatomy as will be appreciated by persons of ordinary skill in the art having the benefit of the instant disclosure. The rib contact surface 160 may be substantially flat, concave, convex, irregularly shaped, and may have a first portion having a first curvature or shape, and a second portion, having a second curvature or shape, for example.

In an exemplary embodiment of the inventive concepts disclosed herein, one or more of the rib contact surface 160, the cradle 156, and the rib cradle insert 114 may be constructed of PEEK, although other materials having a tensile modulus, a hardness, or other mechanical properties similar of substantially identical to the hardness of cortical bone, for example, may be used.

Referring now to FIGS. 9-10, the cradle end half 116 may include a tongue 164 and a cradle portion 166.

The tongue 164 may be configured to be slidably received into the slot 136 of the base member 110, for example. The tongue 164 may include an opening 168 formed therein, the opening 168 may be sized and configured to correspond to the opening 138 and to align with the opening 138 when the tongue 164 is inserted into the slot 136, such that the pin 140 of the lock 118 may be received therethrough, to secure the connection between the cradle end half 116 and the base member 110, for example. The tongue 164 may include an end 170 that has a substantially V-shaped notch 172 formed therein, the notch 172 configured to correspond to the crest 142, such that the crest 142 may be received into the notch 172 when the tongue 164 is inserted into the slot 136, to secure the connection between the tongue 164 and the base member 110, for example. It is to be understood, that in some exemplary embodiments of the inventive concepts disclosed herein, the notch 172, and the crest 142 may be omitted or may be replaced with other features configured to secure the connection between the tongue 164 and the base member 110, as will be appreciated by persons of ordinary skill in the art.

The cradle portion 166 may include a hook-like protrusion 174 having an end 176. The protrusion 174 may be configured such that the protrusion 174 forms a substantially circular ring with the rib cradle insert 114 by positioning the end 176 adjacent to the end 162, for example, such that the rib connector 102 substantially encloses, substantially encircles, or substantially cradles a patient's rib therein. The cradle portion 166 may further include one or more grasping notches 178 formed therein. The one or more grasping notches 178 may be implemented similarly to the grasping notches 128, and may be configured to allow a surgical tool to securely grasp the cradle end half 116 during surgical procedures, for example.

The cradle end half 116 may be constructed of any suitable material, such as surgical steel, titanium, metals, alloys, plastics, PEEK, resins, ceramics, and combinations thereof, for example.

Figure 11:
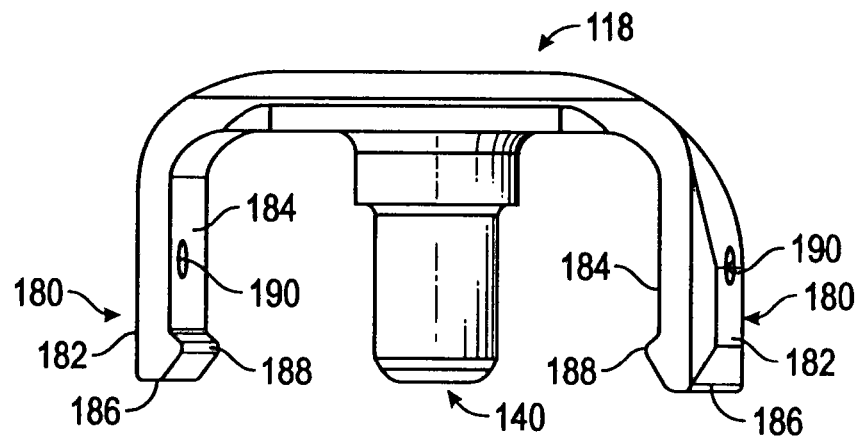
FIG. 11 is a perspective view of a lock.

Referring now to FIG. 11, the lock 118 may be generally shaped as a C-shaped clamp and may include a central shear pin 140 and two legs 180 spaced at a distance from the pin 140, for example. The legs 180 may have external surfaces 182, internal surfaces 184, and ends 186, and a shoulder 188 formed in the internal surfaces 184 adjacent to the end 186. The shoulder 188 may be configured to engage or snap around the attachment end 154 of the rib cradle insert 114, for example. The lock 118 may engage and secure multiple components of the rib connector 102, for example, by inserting the pin 140 through the opening 138, such that the legs 180 may grasp the cradle end half 116 and the rib cradle insert 114, for example.

The lock 118 may further comprise one or more grasping notches 190 extending through the legs 180, for example. The one or more grasping notches 190 may be implemented similarly to grasping notches 128 and may be configured to allow for a surgical tool (not shown) to securely grasp the lock 118 during surgical procedures, for example. The one or more grasping notches 190 may be configured to allow a surgical tool (not shown) to laterally open the legs 180, such that the shoulder 188 may release the lock 118, and allow for the lock 118 to be inserted or removed, for example.

Figure 12:
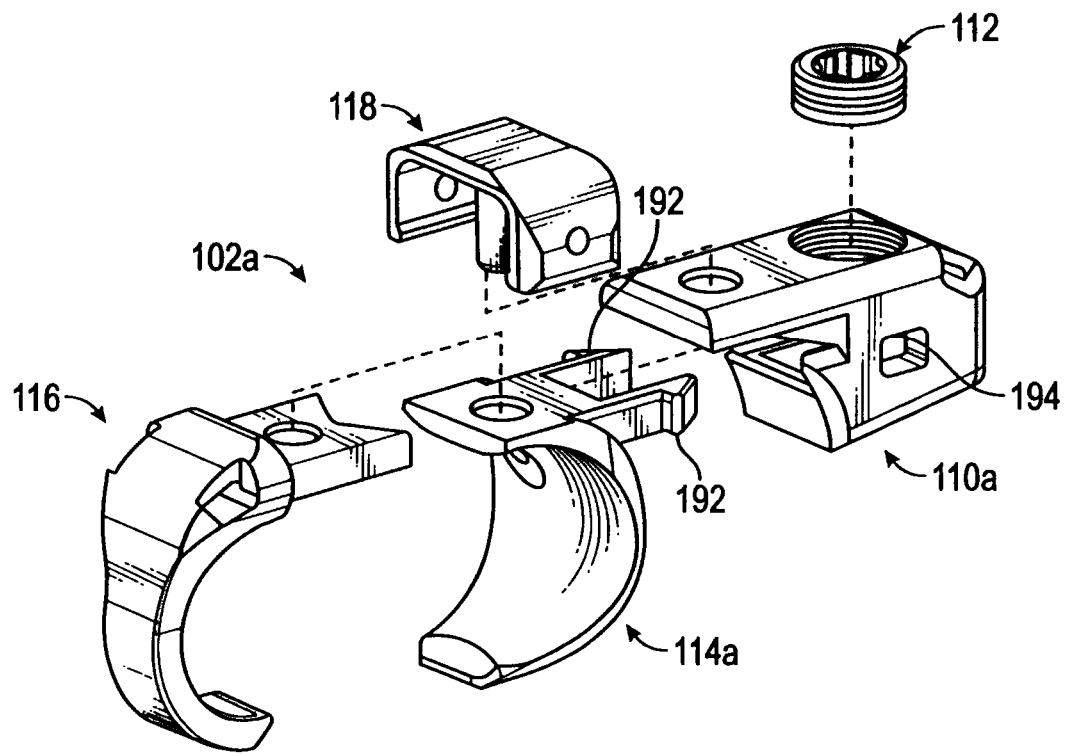
FIG. 12 is an exploded, perspective view of another embodiment of a rib connector.
Figure 13:
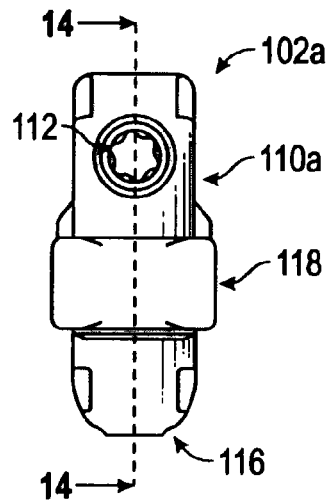
FIG. 13 is a top plan view of the rib connector of FIG. 12.
Figure 14:
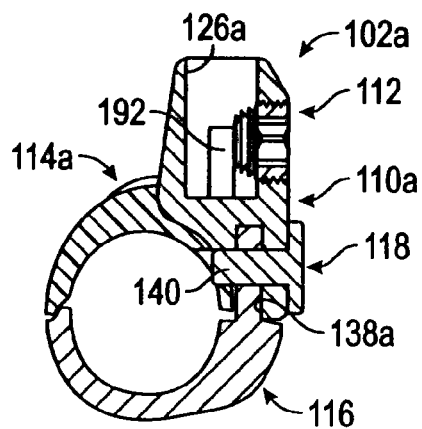
FIG. 14 is a cross-sectional view along line 14-14 of FIG. 13.

Referring now to FIGS. 12-14, another embodiment of a rib connector 102a is shown therein. The rib connector 102a may include a base member 110a, a set screw 112, a rib cradle insert 114a, a cradle end half 116, and a lock 118. The rib connector 102a may be implemented similarly to the rib connector 102, except that the rib cradle insert 114a may be implemented as a snap-in rib cradle insert 114a, rather than using a radial track, as described above, for example.

The rib cradle insert 114a may include two bilateral cantilever snap-in arms 192, which may be configured to fit inside corresponding attachment notches 194 formed into the base member 110a, such that the rib cradle insert 114a may be attached to the base member 110a and a slot 136a (FIG. 14) may be defined by the rib cradle insert 114a and the base member 110a, for example. The attachment notches 194 may intersect an opening 126a, such that the arms 192 fit substantially level with the opening 126a, so as not to obstruct the opening 126a, for example. As will be understood by a person of ordinary skill in the art, a portion of the adjustable rod assembly 106 inserted into the opening 126a may prevent the arms 192 from being removed from the attachment notches 194, for example, by pressing or otherwise securing the arms 192 into the attachment notches 194.

The set screw 112, the lock 118, and the cradle end half 116 have been described above and will not be described herein in detail. The set screw 112, the cradle end half 116, and the lock 118 may be modular components and may be interchangeable between the rib connector 102 and the rib connector 102a, for example.

Figure 15:
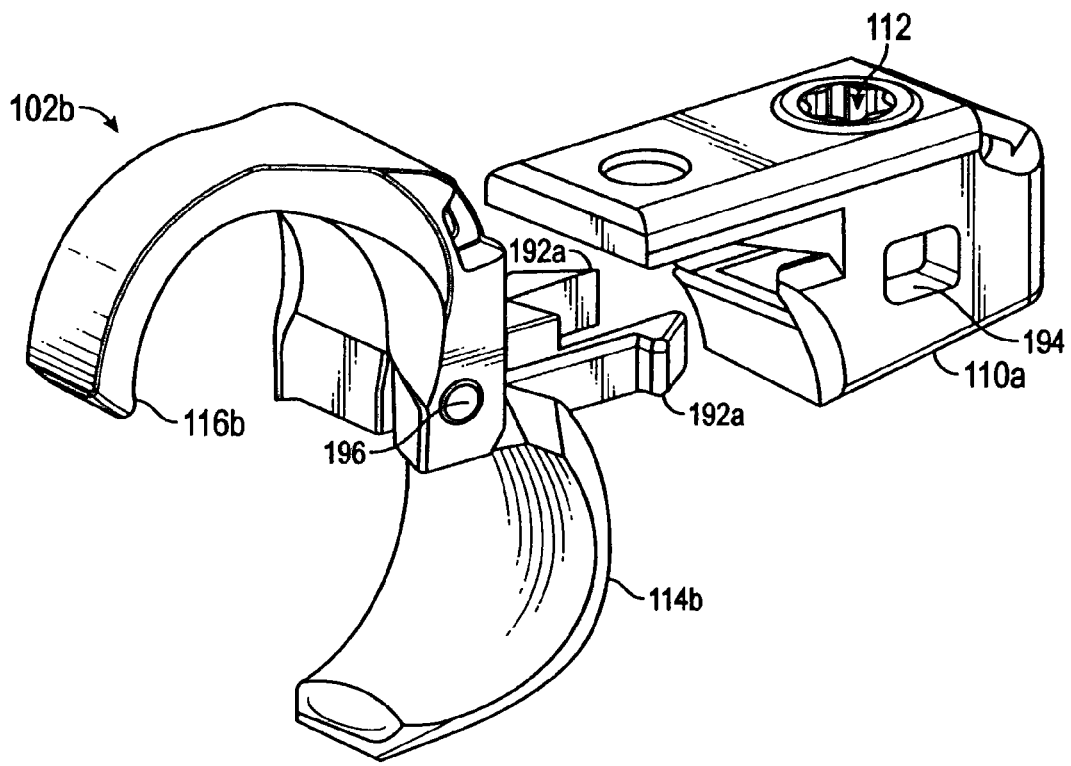
FIG. 15 is a perspective view of another embodiment of a rib connector.

Referring now to FIG. 15, shown therein is an exemplary embodiment of a rib connector 102b according to the inventive concepts disclosed herein. The rib connector 102b may be implemented similarly to the rib connector 102, and may include a base member 110a, a set screw 112, a rib cradle insert 114b, and a cradle end half 116b. The lock 118 has been omitted in this embodiment as will be described below.

The base member 110a, the set screw 112, and the lock 118 have been described above and will not be described in detail herein, except to describe their function in the rib connector 102b.

The rib connector 102b may include a rib cradle insert 114b implemented as a snap-in rib cradle insert 114b, including two bilateral cantilever snap-in arms 192a, which may be configured to fit inside corresponding attachment notches 194 formed into the base member 110a. Further, the cradle end half 116b may be pivotally connected with the rib cradle insert 114b, such as via one or more pin 196, or in any other desired manner, for example, to allow for the rib cradle insert 114b and the cradle end half 116b to pivot away from one another to receive a patient's rib therebetween, and to pivot towards one another to substantially enclose, substantially encircle, or substantially cradle the patient's rib, for example.

As will be appreciated by persons of ordinary skill in the art, once the arms 192a of the rib cradle insert 114b are inserted into the corresponding notches 194a of the base member 110b, the cradle end half 116b is likewise attached to the base member 110b, and the lock 118 may be omitted.

Figure 16:
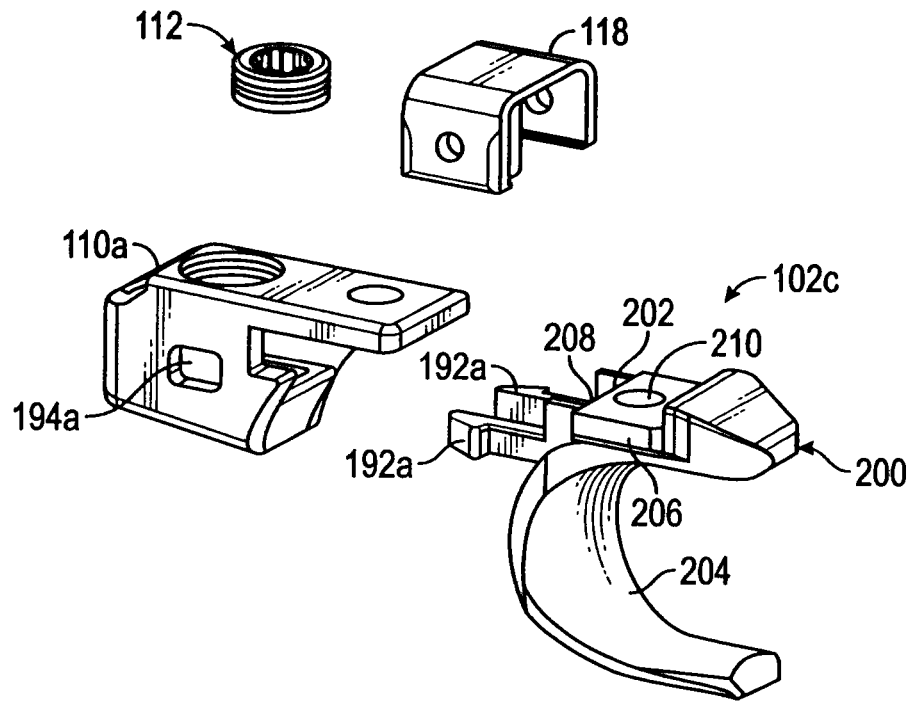
FIG. 16 is an exploded perspective view of another embodiment of a rib connector.
Figures 17, 18:
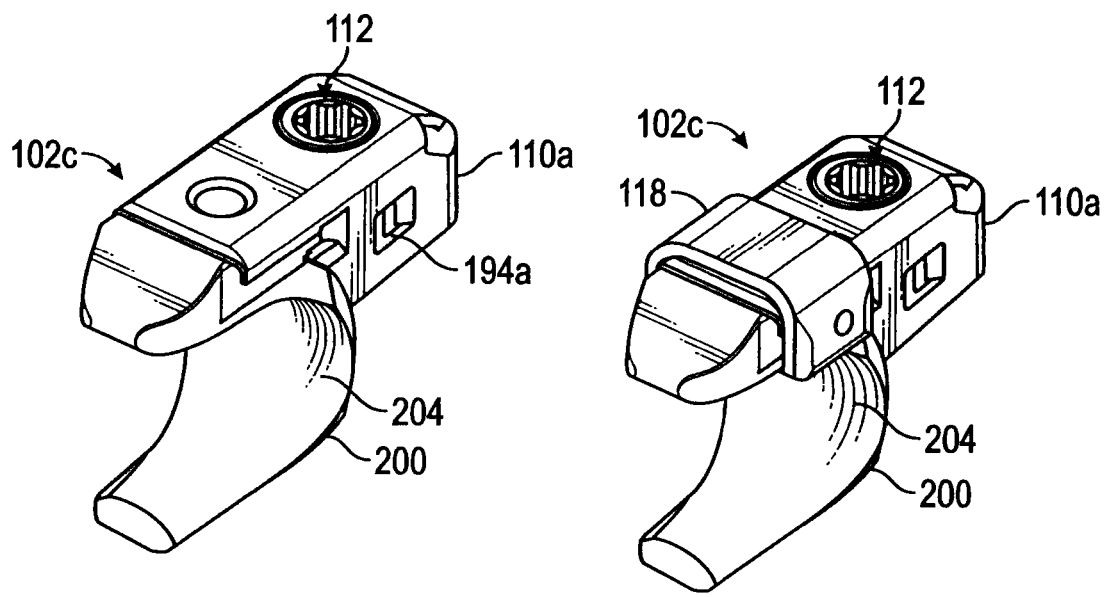
FIG. 17 is a perspective view of the rib connector of FIG. 16 with the lock removed for clarity.
FIG. 18 is a perspective view of the rib connector of FIG. 16 with the lock shown.

Referring now to FIGS. 16-18, shown therein is an exemplary embodiment of a rib connector 102c. The rib connector 102c may include a base member 110a, a set screw 112, an optional lock 118, and a rib cradle insert 114c.

The base member 110a, the set screw 112, and the lock 118 have been described above and will not be described in detail herein, except to describe their function in the rib connector 102c.

The rib cradle insert 114c may be implemented similarly to the rib cradle insert 114 and may include a rib cradle 200, and an attachment end 202.

The rib cradle 200 may be a hook-like structure having a rib contact surface 204, for example. The rib contact surface 204 may be constructed and implemented similarly to the rib contact surface 160 of the cradle insert 114 as described above, for example. The rib contact surface 204 is desirably constructed of an implantable plastic such as PEEK, or from any other material having mechanical properties (e.g., hardness, tensile modulus, or resiliency) substantially similar to the mechanical properties of human cortical bone, as described above, for example.

The attachment end 202 may include two bilateral cantilever snap-in arms 192a, which may be configured to fit inside corresponding attachment notches 194a formed into the base member 110a, such that the rib cradle insert 114c may be attached to the base member 110a as described above, for example. The attachment end 202 may further include a portion 206 configured to substantially fill the slot 136a. The portion 206 may include a v-shaped notch 208 configured to receive the crest 142 therein, such that the rib cradle insert 114c may be securely attached to the base member 110a, for example.

As will be appreciated by persons of ordinary skill in the art, once the snap-in arm 192a are inserted into the attachment notches 194a, the lock 118 may be inserted through an opening 210 in the attachment end 202 to secure the rib cradle insert 114c to the base member 110a. Further, in some exemplary embodiments, a portion of the adjustable rod assembly 106 may be inserted into the base member 110a, such that the portion of the adjustable rod assembly 106 secures the rib cradle insert 114c and the base member 110a, in which case the lock 118 may be omitted as desired.

Due to the fact the rib connector 102c only partially encircles a patient's rib, the rib connector 102c may be used in combination with a rib connector 102, which completely encircles the patient's rib as described above, in some exemplary embodiments, for example. Further, in some exemplary embodiments of the inventive concepts disclosed herein, one or more rib connector 102, one or more rib connector 102a, one or more rib connector 102b, one or more rib connector 102c, and combinations thereof may be used with an bone support apparatus 100, whether such bone support apparatus 100 is implemented as a rib-to-pelvis device, a rib-to-spine device, or a rib-to-rib device as will be appreciated by persons of ordinary skill in the art.

It is to be understood that in some exemplary embodiments of a rib connector 102 according to the inventive concepts disclosed herein, a variety of optional anti-lateral migration features may be implemented in the rib contact surface 160, including knurled rib contact surfaces (not shown), spiked rib contact surfaces (not shown), sharp ridges (not shown), or bone screws (not shown), and combinations thereof. Sharp edge ridges (not shown) may prevent lateral migration of a rib connector 102 according to the inventive concepts disclosed herein by biting into the rib as the angle of the rib connector 102 changes, for example.

Further, in some exemplary embodiments of the inventive concepts disclosed herein, the contact surface 160 of a rib connector 102 may be configured to be asymmetric (not shown), such as having an asymmetric shape to accommodate for left or right ribs, or having a variety of angles, and combinations thereof, for example.

Embodiments of a rib connector 102 according to the inventive concepts disclosed herein may be configured to improve the anchoring on the bone support apparatus 100 to the ribs and may utilize modular components that may be interchanged with other areas of the bone support apparatus 100, for example.

Figure 20:
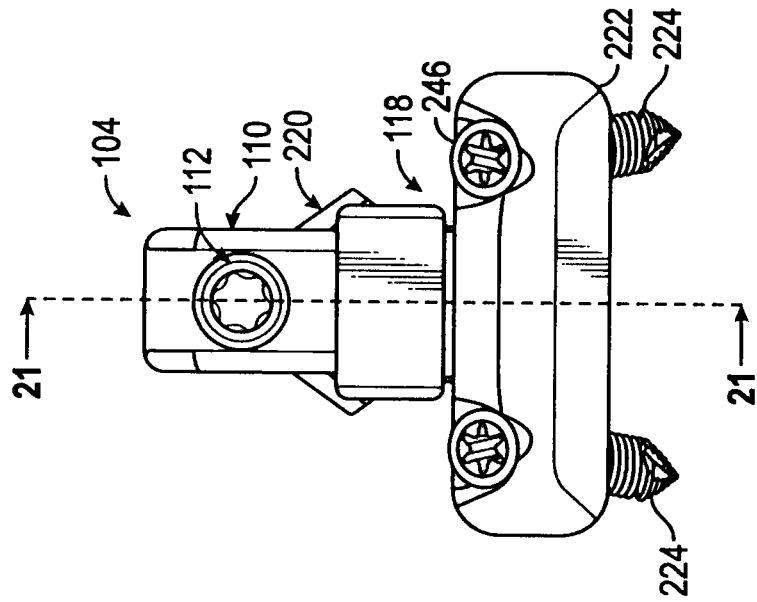
FIG. 20 is a top plan view of the ilium connector of FIG. 19.
Figure 19:
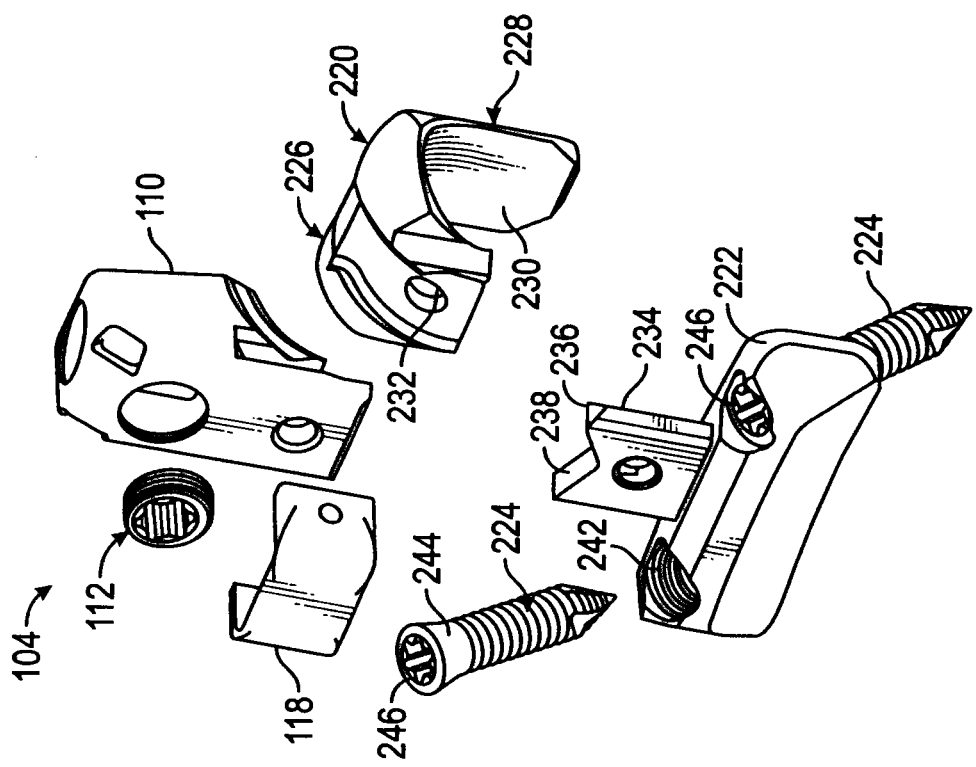
FIG. 19 is an exploded perspective view of an ilium connector.
Figure 21:
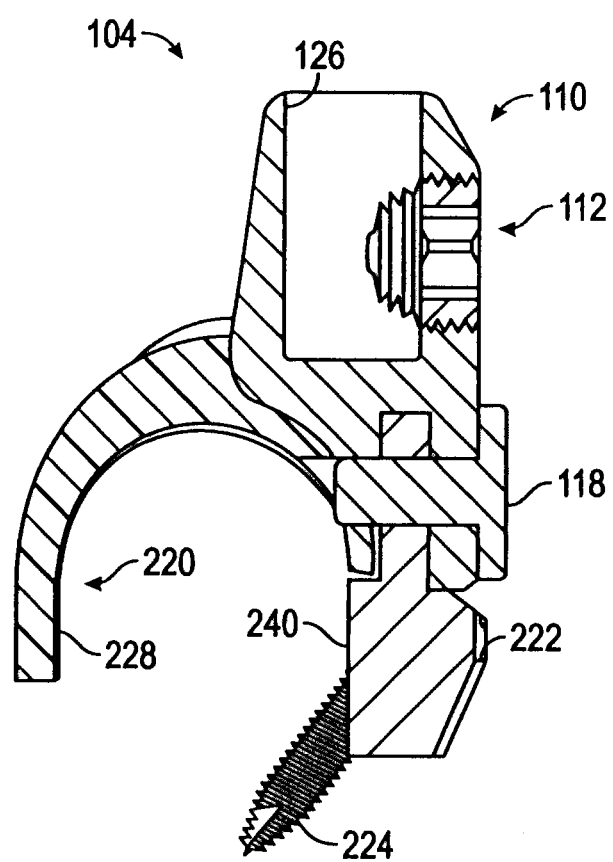
FIG. 21 is a cross-sectional view along line 21-21 of FIG. 20.

Referring now to FIGS. 19-21, an exemplary embodiment of an ilium connector 104 according to the inventive concepts disclosed herein includes a base member 110, a set screw 112, an ilium cradle insert 220, an ilium plate 222, one or more conical bone screw 224, and a lock 118.

The base member 110, the set screw 112, and the lock 118 may be modular components that may be interchanged with the rib connector 102, for example, and will not be described in detail herein, except to describe their function in connection with the ilium connector 104.

The ilium cradle insert 220 may be implemented similarly to the rib cradle insert 114, and may include an attachment end 226 and a cradle 228. The ilium cradle insert 220 may be implemented in a variety of shapes and sizes that may be interchangeable by a surgeon as desired, or as determined by patient anatomy, for example.

The attachment end 226 may be implemented similarly to the attachment end 154 and is configured to allow the ilium cradle insert 220 to be selectively attached to the base member 110 as described above with reference to the rib connector 102, for example.

The cradle 228 may be implemented as a hook-like structure having a bone contact surface 230 constructed from any suitable implantable plastic having mechanical properties (e.g., resiliency or hardness) similar to human bone, such as PEEK, for example. The material from which the cradle 228 is constructed may include any biocompatible material that has mechanical properties (e.g. hardness or Young's modulus) substantially similar to the mechanical properties of human bone. For example, human cortical bone may generally have a Young's (or tensile) modulus of 14 gigapascals (GPa), and the material selected for the construction of the cradle 228 may have a Young's modulus varying from about 4 to about 24 GPa, from about 10 to about 20 GPa, from about 12 GPa to about 16 GPa, or substantially equal to 14 GPa, and combinations thereof, for example.

The bone contact surface 230 may be implemented in multiple configurations configured to correspond to different anatomy found on the ilium crest of a patient, for example. In some exemplary embodiments, the bone contact surface 230 may include a curvature, or may be substantially straight depending on patient anatomies, for example. In some exemplary embodiments, the bone contact surface 230 may have one or more of a first portion having a first curvature, a second portion being substantially straight, a third portion having a second curvature, and combinations thereof, for example.

An opening 232 may be formed in the cradle 228, the opening 232 configured to receive the pin 140 of the lock 118 therein, for example.

The ilium plate 222 may include a tongue 234 having an end 236 with a V-shaped notch 238 configured to interface with the crest 142 of the base member 110, for example. The ilium plate 222 may also include a convex ilium interface 240 configured to substantially correspond to the shape and size of the ilium of a patient, for example. The ilium plate 222 may further include one or more distally-anterior directed threaded holes 242. The one or more holes 242 may have a female conical locking thread configured to receive one or more bone screw 242 therein such that the ilium plate 222 may be secured to a patient's ilium with the one or more bone screw 224, for example.

The one or more bone screw 224 may be implemented as any suitable surgical screw having a male conical locking head 244 with internal drive feature 246.

The one or more bone screw 224 may include a bi-cortical thread profile to allow for the one or more bone screw 224 to be inserted into a patient's ilium at any suitable angle, for example. A drill guide (not shown) and a drill (not shown) may be used to drill one or more openings into a patient's ilium at any desired angle, to position the one or more bone screw 224 at any suitable angle in a patient's ilium. The female conical locking thread of the one or more holes 242 and the male conical locking head 244 may cooperate to allow the one or more bone screw 224 to be threaded into the one or more holes 242 at any desired angle, as will be appreciated by a person of ordinary skill in the art. For example, the bone screw 224 may be threaded into the one or more holes 242 at an angle varying from about 0° to about 90°.

In some exemplary embodiments, where two or more bone screws 224 are implemented, a first bone screw 224 and a second bone screw 224 may be oriented at any angle relative to one another varying from being substantially parallel to one another, to any desired angle including being substantially perpendicular to one another. Further, a first bone screw 224 may be inserted into a patient's ilium at a first angle, and a second bone screw 224 may be inserted into the patient's ilium at a second angle, and the first and the second angle may be different, substantially similar, or substantially equal to one another, for example.

The internal drive feature 246 may be implemented as any desired surgical drive configured to allow a surgical tool to interface with the internal drive feature 246 and drive the bone screw 224, such as a Phillips drive, a hexagonal drive, a star-shaped drive, a square drive, and combinations thereof, for example.

The ilium connector 104 may be implanted surgically at any desired location on a patient's ilium similarly to the current S-hook device, for example.

The lock 118 may be implemented as described above and may function to securely lock the components of the ilium connector 104 to one another, for example.

The set screw 112 may be implemented and may function substantially as described above.

In some exemplary embodiments, the modular design of the ilium connector 104 may be modified to work without the lock 118, for example. Further, the shape and number of holes 242 in the ilium plate 222 may be modified as desired.

As will be appreciated by persons of ordinary skill in the art, rather than contacting the crest of the patient's ilium, and ilium connector 104 according to the inventive concepts disclosed herein is configured to contact the crest of the ilium, but is also provided with one or more posterior attachment points to the ilium wall via the one or more bone screw 224, and cradles the anterior ilium wall via the cradle 228, for example.

Referring now to FIGS. 22-23, an exemplary embodiment of an adjustable rod assembly 106 according to the inventive concepts disclosed herein may have a thoracic segment (or member) 250 and a lumbar segment (or member) 252 connected by an expansion segment (or member) 254, and one or more lock 256. A plurality of openings in the expansion segment 254 may be aligned with a plurality of openings in each of the thoracic segment 250 and the lumbar segment 252 to allow for the insertion of the one or more lock 256 therethrough, such that the length of the adjustable rod assembly 106 may be adjusted, as will be described herein below.

The thoracic segment 250 may have a rod portion 258 configured to be selectively inserted into the rib connector 102 and an expansion portion 260 defining a C-shaped thoracic female channel 262 configured to slidably receive a male end of the expansion segment 254 therein, as will be described herein below. The thoracic segment 250 may have a typical thoracic radius as shown in FIG. 22 (e.g., a typical healthy patient's thoracic radius), and may include any desired curvature relative to a longitudinal axis thereof, to accommodate varying patient anatomies, for example. It is to be understood that the thoracic segment 250 may be substantially straight, or may include a first portion having a first curvature, and a second portion being substantially straight or having a second curvature, for example. The curvature of the thoracic segment 250 may be adjusted by the surgeon, such as by using a bending surgical tool (not shown) to adjust the curvature of the thoracic segment 250, for example. The thoracic segment 250 may be constructed of any suitable material, such as titanium, stainless steel, plastics, ceramics, and combinations thereof, for example. In some exemplary embodiments of the inventive concepts disclosed herein, the thoracic segment 250 may be constructed of a durable rigid material capable of withstanding the typical forces experienced by the thoracic segment during use.

Figure 24:
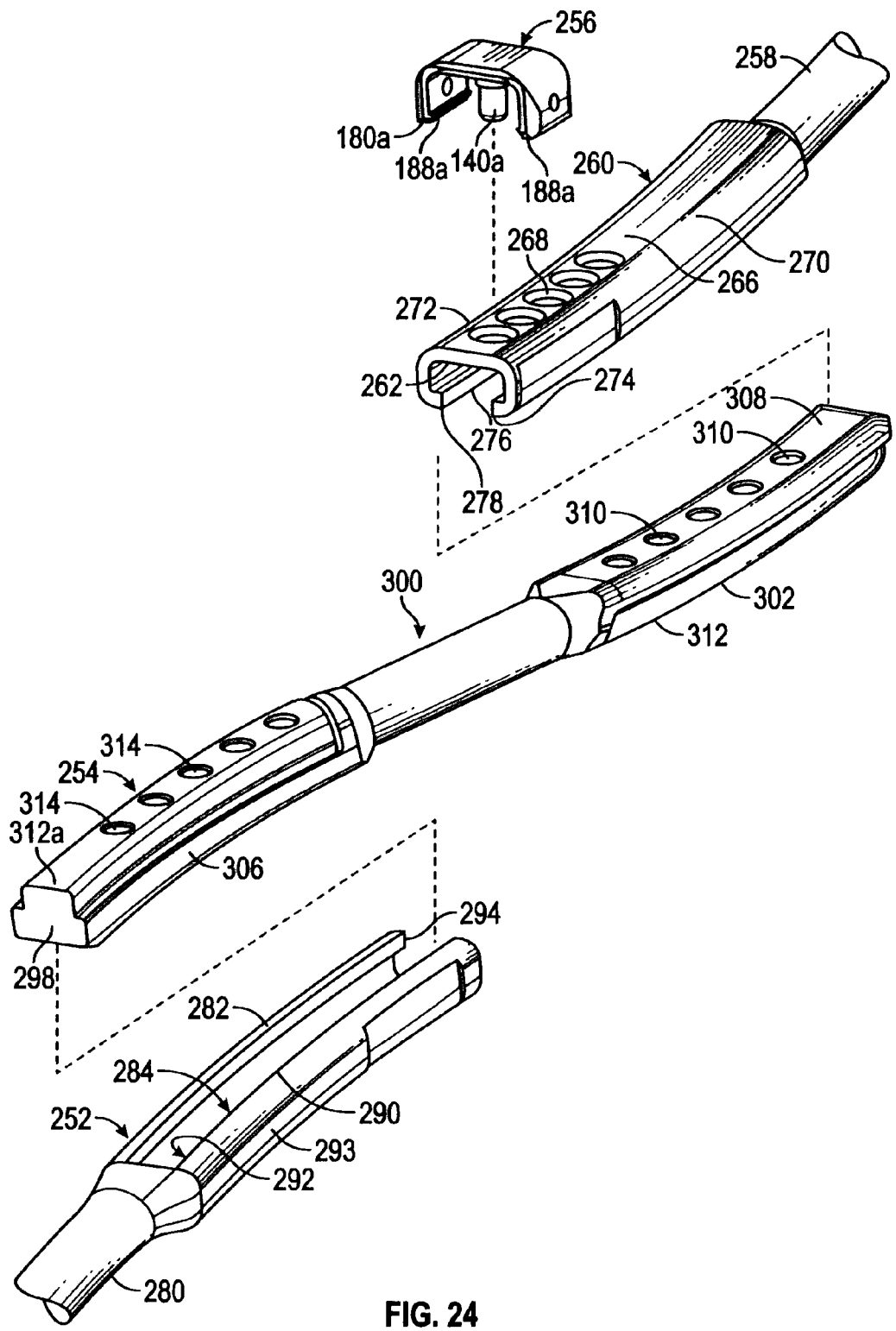
FIG. 24 is an exploded perspective view of the adjustable rod assembly of FIG. 22.

Referring now to FIG. 24, the rod portion 258 may be substantially cylindrical and may be configured to correspond to the opening 126 of the rib connector 102, such that an end 264 may be inserted into the opening 126 to attach the thoracic segment 250 to the rib connector 102, for example. The set screw 112 may be partially advanced into the opening 126 such that the set screw 112 applies transverse compressive force to the end 264 to secure the connection between the end 264 of the thoracic segment 250 and the rib connector 102, and to substantially prevent rotation of the end 264 inside the opening 126, for example. As will be understood, prior to advancing the set screw 112 into the opening 126, the rib connector 102 and the thoracic segment 250 may be rotated relative to one another to any desired position or angle, depending, for example, on patient anatomy.

The substantially C-shaped thoracic female channel 262 may have a top surface 266 defining one or more adjustment openings 268 therein, a pair of side surfaces 270 and 272, and a bottom surface 274 defining a longitudinal opening 276 therein. The longitudinal opening 276 may intersect an end 278 of the thoracic female channel 262, for example. The side surfaces 270 and 272 may be configured such that legs 280 of the lock 256 may grasp the side surfaces 270 and 272, for example, to secure the lock 256 in place.

The adjustment openings 268 may be spaced apart a distance from one another and may be configured to receive a pin 140a of the lock 256 therein. It is to be understood that in some exemplary embodiments a single adjustment opening 268 may be implemented, while in other exemplary embodiments a plurality of adjustment openings 268 may be implemented. Further, in some embodiments where more than two adjustment openings 268 are implemented, the distance between a first adjustment opening 268 and a second adjustment opening 268 may be greater than, lesser than, or substantially equal to the distance between the second adjustment opening 268 and a third adjustment opening 268, for example. The one or more adjustment openings 268 may accept the pin 140a of the lock 256 from the direction of the top surface 266 or from the direction of the bottom surface 274, for example.

The thoracic segment 250 may be constructed of any suitable biocompatible material, such as surgical steel, titanium, metals, alloys, ceramics, resilient plastics, thermoplastics, non-metals, resins and combinations thereof, for example.

The lumbar segment 252 may be implemented similarly to the thoracic segment 250 and may include a rod portion 280 adapted to be inserted into the ilium connector 104, and an expansion portion 282 defining a C-shaped lumbar female channel 284 configured to slidably receive a lumbar end of the expansion segment 254 therein, as will be described herein below. In some exemplary embodiments of the inventive concepts disclosed herein, the lumbar segment 252 and the thoracic segment 250 may be substantially identical and may be interchangeable with one another, as will be appreciated by persons of ordinary skill in the art.

The rod portion 280 may be implemented similarly to the rod portion 258 and may be substantially cylindrical such that it may have an end 264a configured to be at least partially inserted into the ilium connector 104, for example. The lumbar segment 252 may have a typical lumbar curvature as shown in FIG. 22, or may have any desired curvature which may be adjusted similarly to adjusting the curvature of the thoracic segment 250 as described above, for example.

The expansion portion 282 may likewise have a typical lumbar radius as shown in FIG. 22, for example, and may have an adjustable radius as described above.

The substantially C-shaped lumbar female channel 284 may have a top surface 286 defining one or more adjustment openings 288, and a bottom surface 290 defining a longitudinal opening 292 and having two side surfaces 293. The longitudinal opening 292 may intersect an end 294 of the lumbar female channel 284, for example.

The lumbar female channel 284 may be configured to slidably receive a male end of the expansion segment 254 therein. The one or more adjustment openings 288 may be implemented similarly to the one or more adjustment openings 268, for example.

Figure 25:
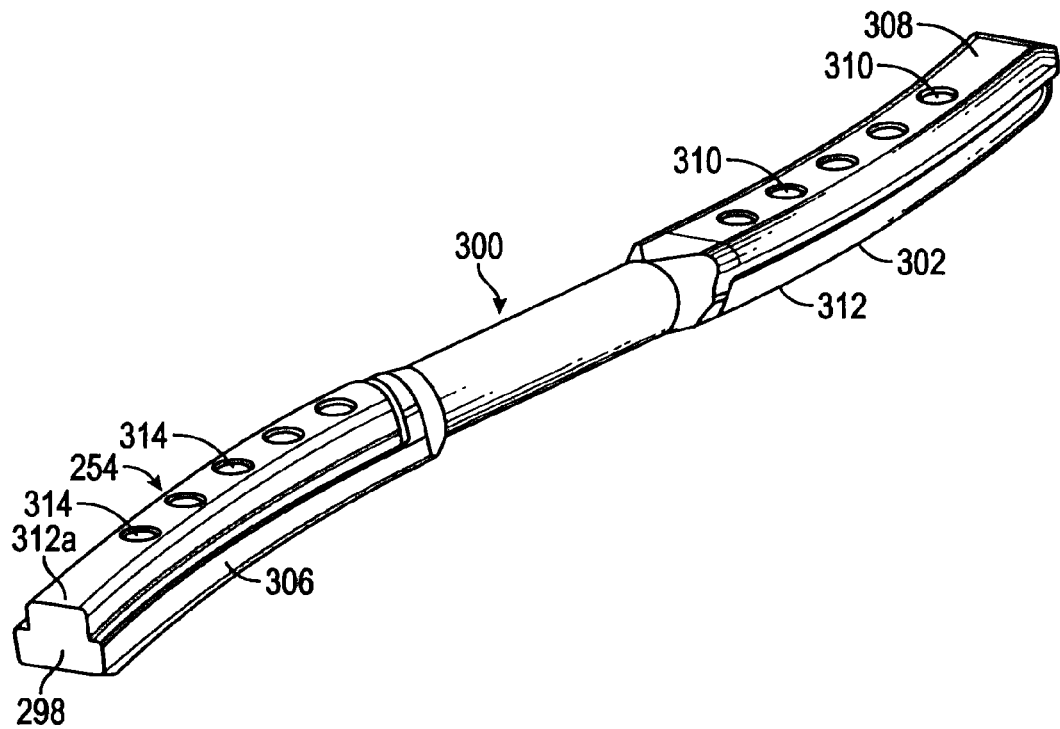
FIG. 25 is a perspective view of an expansion segment of the adjustable rod.
Figure 26:
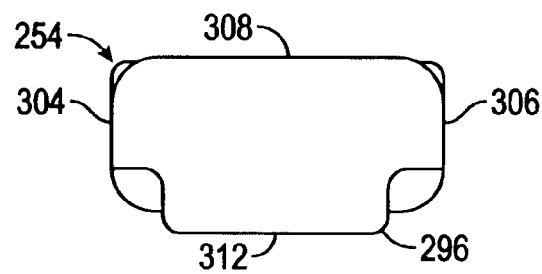
FIG. 26 is an end view of the expansion segment of FIG. 25.

Referring now to FIGS. 25 and 26, the expansion segment 254 may be implemented as an elongated body having a thoracic male end 296, a lumbar male end 298, and a middle portion 300 connecting the thoracic male end 296 and the lumbar male end 298. The expansion segment 254 may be constructed of a flexible resilient material such as PEEK, or PEEK with carbon fiber inserts to stiffen the flexion as desired, and may be configured to flex and absorb shocks from normal activities that a patient implanted with the bone support apparatus 100 may encounter. The material from which the expansion segment 254 is constructed may include any biocompatible material that has mechanical properties (e.g., hardness, or tensile/Young's modulus) substantially similar to the mechanical properties of human bone. For example, human cortical bone may generally have a Young's (or tensile) modulus of 14 gigapascals (GPa), and the material selected for the construction of the expansion segment 254 may have a Young's (or tensile) modulus varying from about 4 to about 24 GPa, from about 10 to about 20 GPa, from about 12 GPa to about 16 GPa, or substantially equal to 14 GPa, and combinations thereof, for example.

It is to be understood that in some exemplary embodiments, the expansion segment 254 may be constructed of a rigid material, such as titanium or titanium alloy, for more rigid indications. Further, in some exemplary embodiments, the thoracic male end 296, the lumbar male end 298, and the middle portion 300 may be constructed as a unitary body.

The thoracic male end 296 may be implemented as a male protrusion corresponding to the thoracic female channel 262, such that the thoracic male end 296 may be slidably inserted into the thoracic female channel 262 via the end 278. The thoracic male end 296 may include an outer surface 302, a first side surface 304 and a second side surface 306, and an inner surface 308 that combine to define a T-bar shape when the thoracic male end 296 is viewed in an end view (FIG. 26). The thoracic male end 296 may include one or more openings 310 extending from the outer surface 302 to the inner surface 308, the openings 310 sized and positioned such that the openings 310 may align with the one or more adjustment openings 268 and may receive the pin 140a of the lock 256 therethrough, for example, to secure the position of the thoracic male end 296 relative to the thoracic female channel 262. The thoracic male end 296 may define a longitudinal protrusion 312 configured such that the longitudinal protrusion 312 fits in the open end of the thoracic female channel 262 to substantially prevent the rotation of the thoracic male end 296 inside the thoracic female channel 262, for example. The openings 310 may extend through the longitudinal protrusion 312, for example. The thoracic male end 296 may also have a typical thoracic curvature configured to correspond to the curvature of the thoracic female channel 262, for example.

The lumbar male end 298 may be implemented as a male protrusion corresponding to the lumbar female channel 284, such that the lumbar male end 298 may be slidably inserted into the lumbar female channel 284 via the end 294. The lumbar male end 298 may include one or more openings 314 formed therethrough, the openings 314 sized and positioned such that the openings 314 may align with the one or more adjustment openings 288 and may receive the pin 140a of the lock 256 therethrough, for example, to secure the position of the lumbar male end 298 relative to the lumbar female channel 284. The lumbar male end 298 may also have a typical lumbar curvature configured to correspond to the curvature of the lumbar female channel 284, for example. In some exemplary embodiments the lumbar male end 298 may define a longitudinal protrusion 312a, which may be offset at about 180° relative to the longitudinal protrusion 312 of the thoracic male end 296, to allow for the interchangeability of the thoracic segment 250 and the lumbar segment 252, as will be appreciated by persons of ordinary skill in the art.

The middle portion 300 may have any desired cross-section, shape, and thickness, provided that the middle portion 300 is substantially resilient and configured to absorb shock, torsional, compressional, and other forces that may be encountered by the adjustable rod assembly 106 during the normal activities undertaken by the patient, for example. In some exemplary embodiments, the middle portion 300 may include one or more grooves (not shown) or openings (not shown) formed therein, for example.

Referring again to FIG. 24, the lock 256 may be implemented similarly to the lock 118 described above and may have a pin 140a. The lock 256 may be configured to secure the connection between the thoracic segment 250, the lumbar segment 252, and the expansion segment 254, for example.

In some exemplary embodiments of the inventive concepts disclosed herein, the lock 118 and the lock 256 may be substantially identical and may be interchangeable with one another. The lock 256 may have a pin 140a, a pair of legs 180a having shoulders 188a configured to grasp the outside surfaces 170 and 172 of the thoracic female channel 262 and the outside surfaces 293 of the lumbar female channel 284, such that the locks 256 may be secured into position when the pin 140a is inserted into the one or more openings 310 and the one or more adjustment openings 268, and the one or more openings 314 and the one or more adjustment openings 288, for example. The lock 256 may be inserted from either the top surface 286 or the bottom surface 274 of the thoracic female channel 262 and the top surface 286 and the bottom surface 290 of the lumbar female channel 284, as will be understood by persons of ordinary skill in the art.

As will be appreciated by a person of ordinary skill in the art, exemplary embodiments of an adjustable rod assembly 106 according to the inventive concepts disclosed herein may provide surgeons with better control of expansion direction by virtue of having multiple expansion points, which may result in almost double the number of expansions per a given adjustable rod assembly 106 length, which may reduce the number of major surgical revisions as the patient grows. Further, multiple expansion points along an adjustable rod assembly 106 according to the inventive concepts disclosed herein may also provide better directional contrast from previous devices with the addition of the lumbar segment 252. For example, expanding the thoracic segment 250 expansion may push the patient's anterior and expanding the lumbar segment 252 may pull the patient's posterior for a neutral net effect on the patient's body, as will be appreciated by persons of ordinary skill in the art.

In some exemplary embodiments of the inventive concepts disclosed herein, the lock 256 may be omitted and any other suitable locking mechanisms (not shown) may be implemented to secure the components of the adjustable rod assembly 106 to one another and to adjust the adjustable rod assembly 106, for example. For example, a shear pin locking mechanism (not shown), a set screw locking mechanism (not shown), a spring loaded locking mechanism (not shown), a one way ratchet mechanism (not shown), and combinations thereof may be implemented in some embodiments. Further, it will be understood that the male protrusions and the female channels may be reversed, such that the thoracic segment 250 and the lumbar segment 252 have the male protrusions, and the expansion segment 254 has the female channels, for example.

In some exemplary embodiments of the inventive concepts disclosed herein, a first bone connector such as a rib connector 102 may be attached to the thoracic segment 250, and a second bone connector such as a rib connector 102 may be attached to the lumbar segment 252 to allow the adjustable rod assembly 106 to be used in rib to rib constructs, as will be appreciated by persons of ordinary skill in the art. Further, in some exemplary embodiments, other similar bone connectors may be implemented, such as spinal hooks, lamina hooks, pedicle hooks, pelvic hooks, S-shaped pelvic hooks, clamp assemblies, bone screws, pedicle screws, lamina screws, and combinations thereof.

Figure 27:
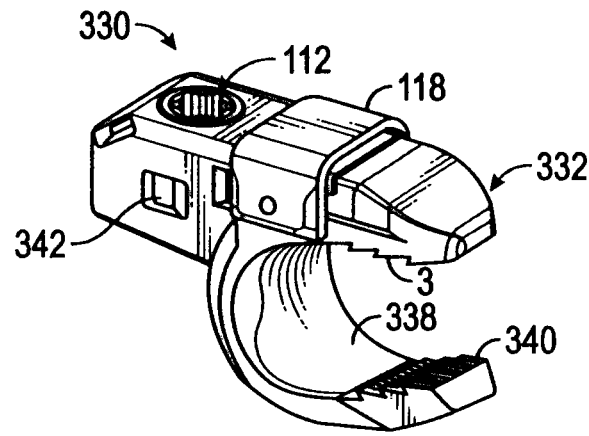
FIG. 27 is a perspective view of an exemplary embodiment of an ilium connector.
Figure 28:
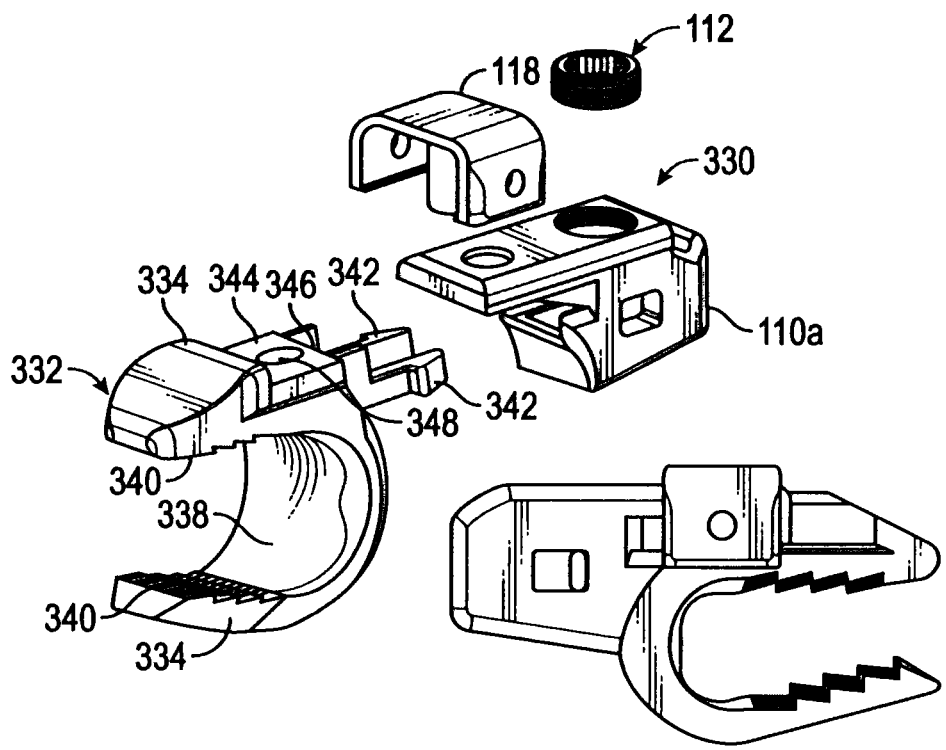
FIG. 28 is an exploded perspective view of the ilium connector of FIG. 27.

Referring now to FIGS. 27-29, shown therein is an exemplary embodiment of an ilium connector 330 according to the inventive concepts disclosed herein. The ilium connector 330 may include a base member 110a, a set screw 112, an optional lock 118, and an ilium cradle 332. The base member 110a, the set screw 112, and the optional lock 118 have been described above and will not be described herein in detail.

The ilium cradle 332 may be implemented similarly to the rib cradle insert 114a, and may be a substantially C-shaped, or substantially U-shaped clamp structure having legs 334, and an attachment end 336, for example. The ilium cradle 332 may be constructed of an implantable plastic such as PEEK, or from any other material having mechanical properties (e.g., hardness, resiliency, or tensile modulus) substantially similar to the mechanical properties of human cortical bone, as described above, for example.

The legs 334 may have ilium contact surfaces 338, for example. The ilium contact surface 338 of the legs 334 may include one or more unidirectional set teeth 340 formed therein and configured to engage a patient's ilium to securely position the ilium cradle 332 onto the patient's ilium, for example.

The attachment end 336 may include two bilateral cantilever snap-in arms 342, which may be configured to fit inside corresponding attachment notches 194a formed into the base member 110a, such that the ilium cradle 332 may be attached to the base member 110a as described above with reference to FIG. 16, for example. The attachment end 336 may further include a portion 344 configured to substantially fill the slot 136a. The portion 344 may include a v-shaped notch 346 configured to receive the crest 142 therein, such that the ilium cradle 332 may be securely attached to the base member 110a, for example. Further, an opening 348 may be formed in the portion 344 and may be configured to receive the pin 140 of the lock 118 therein, for example.

As will be appreciated by persons of ordinary skill in the art, once the snap-in arms 342 are inserted into the attachment notches 194a, the lock 118 may be inserted through an opening 348 in the attachment end 336 to secure the ilium cradle 332 to the base member 110a. Further, in some exemplary embodiments, a portion of the adjustable rod assembly 106 may be inserted into the base member 110a, such that the portion of the adjustable rod assembly 106 secures the ilium cradle 332 and the base member 110a, in which case the lock 118 may be omitted as desired.

Referring now to FIGS. 29-31, to position the ilium connector 330 onto a patient's ilium, the ilium connector 330 may be oriented such that the lock 118 is oriented posterior relative to the ilium. The ilium cradle 332 may be pressed onto the ilium, such as by applying sufficient downwards force as indicated by arrow 350 in FIG. 29 to splay the legs 334 as indicated by arrows 352, such that their respective bone contact surfaces 338 may slide over the ilium crest and come into contact with the posterior and anterior portions of the ilium. The ilium cradle 332 may be pressed in this manner as indicated by arrow 354 in FIG. 30, such that the crest of the ilium abuts the attachment end 336 and the legs 334 may contact the posterior and anterior portions of the ilium, for example. The unidirectional teeth 340 may be set, and the stability of the ilium connector 330 may be checked to ensure secure attachment has been achieved. Pressure may be exerted onto the ilium wall by the legs 334 as indicated by arrows 356 in FIG. 31. The lumbar male end 298 may then be inserted into the base member 110a and secured into place with the set screw 112, for example.

As will be appreciated by a person of ordinary skill in the art, the ilium cradle 332 is connected to the ilium via compressive pressure exerted onto the ilium by the legs 334 via the set teeth 340, for example. To that end, a kit of two or more ilium cradles 332 may be supplied to surgeons, to allow surgeons to select an appropriately sized ilium cradle 332 depending on patient anatomy, to ensure that sufficient contact and pressure is maintained between the patient's ilium and the ilium cradle 332, to minimize, or substantially avoid migration of the ilium cradle 332, for example.

Further, while one or more set teeth 340 have been shown and described herein, exemplary embodiments of an ilium cradle 332 according to the inventive concepts disclosed herein may include other grip-enhancing features (not shown), such as roughened surfaces, bumps, grooves, spikes, striations, knurls, ribs, and combinations thereof, which may be implemented alone, or in various combinations. Further, such grip-enhancing features may be implemented instead of, or in combination with, the one or more set teeth 340, for example.

Further, as will be appreciated by persons of ordinary skill in the art, the lock 118 is optional and may be omitted in some exemplary embodiments of an ilium connector 330 according to the inventive concepts disclosed herein.

An exemplary method of using a bone support apparatus 100 according to the inventive concepts disclosed herein may proceed as follows. One or more appropriate incisions may be made in a patient's body such that access to the implantation sites may be gained by the surgeon. A first bone connector such as the rib connector 102 may be implanted, by substantially encircling or substantially enclosing one or more of the patient's ribs between the rib cradle insert 114 and the cradle end half 116, for example. Similarly, a second bone connector such as the ilium connector 104 may be implanted, by selecting an appropriate location on the patient's ilium and attaching the ilium connector 104 to the patient's ilium by inserting the one or more bone screw 224 into the patient's ilium, for example. One or more other bone connectors may also be implanted as needed or desired by the surgeon, for example.

Next, an adjustable rod assembly, such as the adjustable rod assembly 106, may be implanted by connecting the thoracic portion 250 of the adjustable rod assembly 106 to the rib connector 102. The end 266 of the thoracic segment 250 may be at least partially inserted into the base member 110 of the rib connector 102. The rib connector 102 and the thoracic segment 250 may be oriented at any desired angle relative to one another prior to securing the connection between the thoracic segment 250 and the rib connector 102, such as via advancing the set screw 112 into the opening 126, for example.

The lumbar segment 252 may be similarly connected to the ilium connector 104. The expansion segment 254 may be slidably adjusted to the desired length of the adjustable rod assembly 106, such as by sliding the expansion segment 254 relative to the thoracic segment 250, sliding the expansion segment 254 relative to the lumbar segment 252, and combinations thereof, for example.

The locks 256 may be used to secure the desired position of the adjustable rod assembly 106, such as by inserting the pins 140a of the locks 256 into the adjustment openings 268 and 288, for example.

After the bone support apparatus 100 is secured in the desired position, the incisions may be closed such as via sutures or staples, for example.

As the patient grows, adjustments may be made to the length of the adjustable rod assembly 106, such as by accessing the locks 256, removing the locks 256, adjusting the length of the adjustable rod assembly 106, such as by sliding the thoracic segment 250 relative to the expansion segment 254, or by sliding the lumbar segment 252 relative to the expansion segment 254, and combinations thereof. The locks 256 may then be reinserted into the adjustment openings 268 and 288 to secure the adjustable rod assembly 106 to any desired position. The incisions may then be closed as described above.

Figure 32:
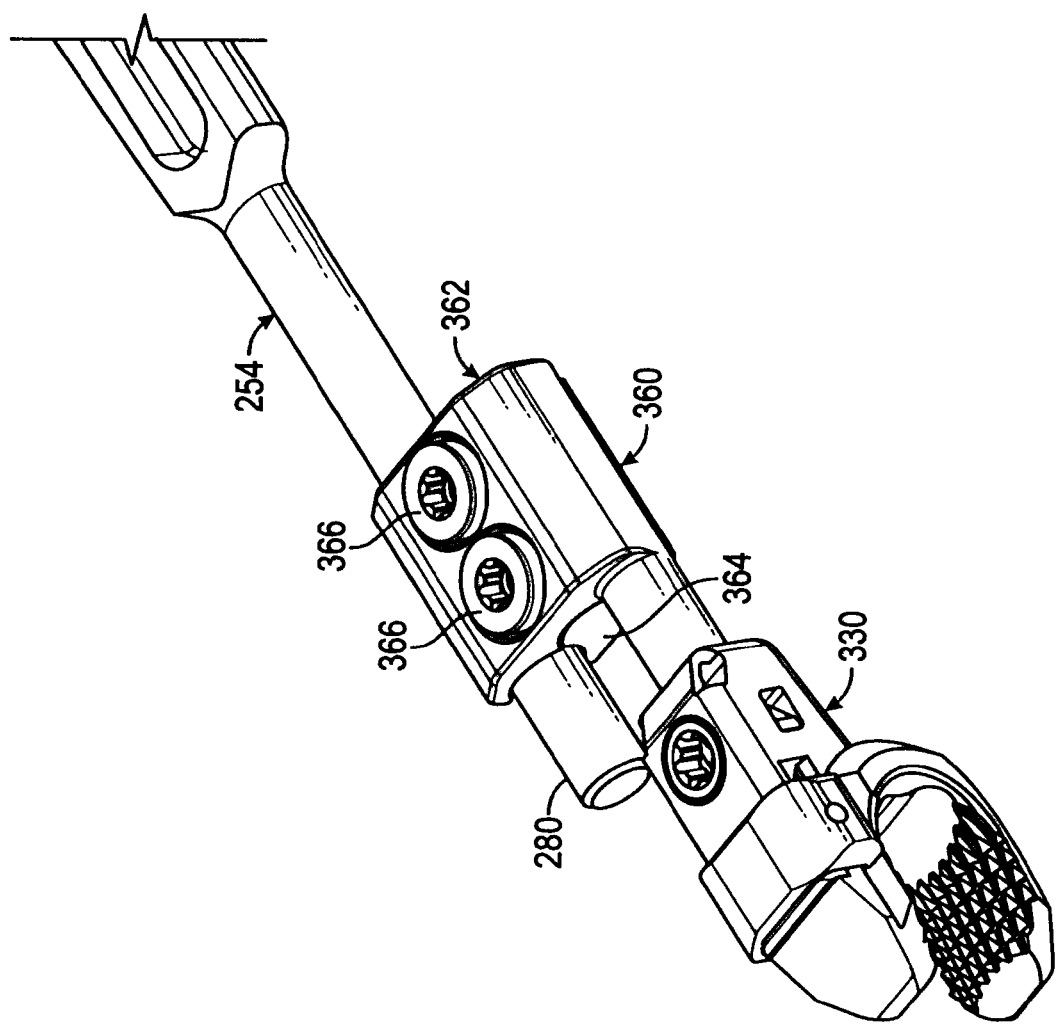
FIG. 32 is a perspective view of an exemplary embodiment of a connector shown connected to an adjustable rod assembly and a rib connector.
Figure 33:
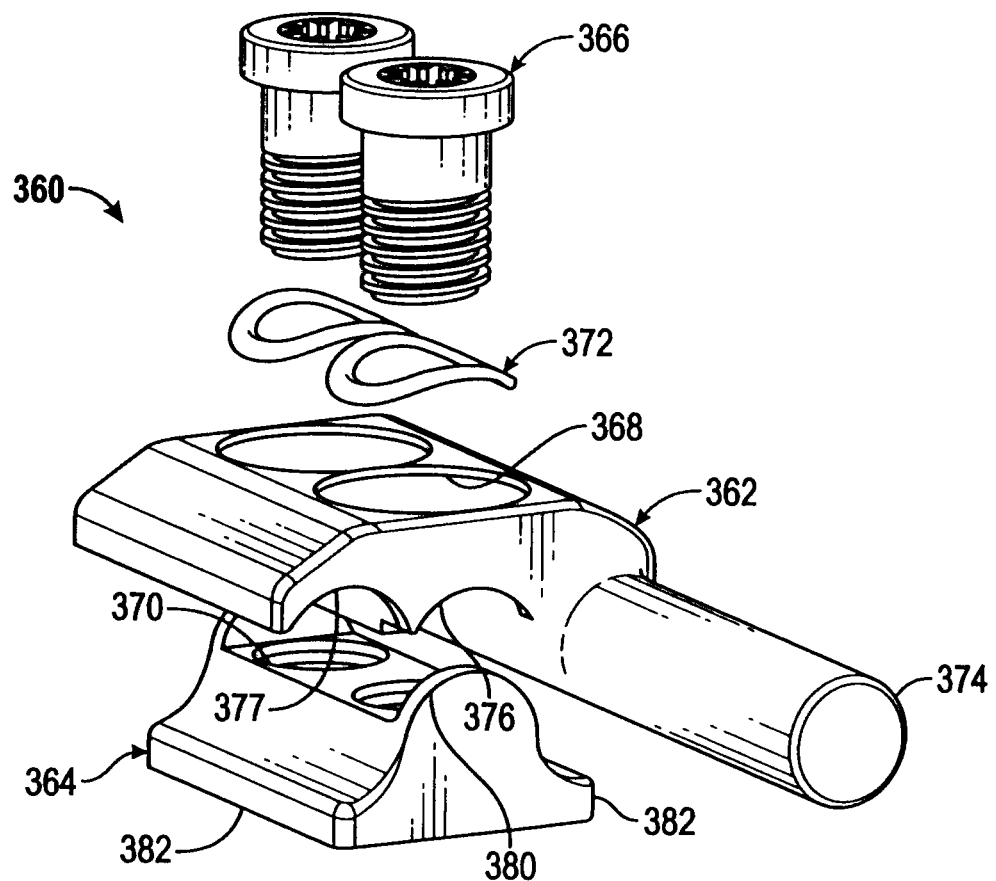
FIG. 33 is an exploded, perspective view of the connector of FIG. 32.

Referring now to FIGS. 32-33, shown therein is an exemplary embodiment of a connector 360 according to the inventive concepts disclosed herein. The connector 360 is shown in FIG. 32 connecting an ilium connector 330 to the lumbar segment 254 of the adjustable rod assembly 106. It is to be understood, however, that the connector 360 according to the inventive concepts disclosed herein may be employed to connect other implements such as a rib connector 102, a rib connector 102a, a rib connector 102b, a rib connector 102c, an ilium connector 104, to the adjustable rod assembly 106, or combinations thereof, for example.

The connector 360 may include a connector body 362 and a clamp member 364. The connector body 362 may be connected with the clamp member 364 via one or more fasteners 366 inserted through openings 368 in the connector body 362 and threadingly inserted through corresponding threaded openings 370 in the clamp member 364, for example. Wave washers 372 constructed of shape-memory material may be implemented with the fasteners 366 to allow a rod portion 258 of the adjustable rod assembly 106 to be inserted into the connector 360 and to maintain slight pressure on the rod portion 258 until the fasteners 366 are tightened, for example.

The connector body 362 may include a rod portion 374, which may be implemented and may function similarly to the rod portion 258 of the thoracic segment 250 or to the rod portion 280 of the lumbar segment 254, for example, so as to allow one or more of the ilium connector 330, the rib connector 102, the rib connector 102a, the rib connector 102b, the rib connector 102c, or the ilium connector 104, and combinations thereof to connect to the rod portion 374, as described above.

The connector body 362 may further include a substantially semi-circular longitudinal notch 376. The notch 276 may be configured to receive a portion of the clamp member 364 therein so as to key the clamp member 364 to the connector body 362. The connector body 362 may further include a substantially semi-circular notch 377 positioned adjacent to the notch 376 and configured to at least partially receive the rod portion 258 or the rod portion 280 therein, for example. While the notch 376 and the notch 377 are shown as being substantially parallel to one another and to the rod portion 374, in some exemplary embodiments, the notch 376 and the notch 377 may be angled relative to one another and/or relative to the rod portion 374 at any desired angle, varying between about 0° and about 90°, for example. The notch 376 and the notch 377 may include friction-enhancing surface features (not shown) such as roughened surfaces, bumps, grooves, striations, and combinations thereof, configured to increase the friction between the notch 376 and the clamp member 364 and between the notch 377 and the rod portion 258 or the rod portion 280, for example, so as to resist or substantially prevent rotation and/or translation of the clamp member 364 and/or the rod portion 258 or 280 relative to the notch 376 and 377. The openings 368 may intersect the notch 376 at any desired location, and the fasteners 366 may extend at least partially through the notch 376 when the fasteners 366 are inserted into the openings 368, for example.

The clamp member 364 may include a protrusion 380 and two tabs 382 positioned on either side of the protrusion 380.

The protrusion 380 may be sized to correspond to the notch 376 so as to be at least partially inserted therein. The protrusion 380 and the notch 376 may optionally include any desired corresponding keying features to ensure an optimal fit between the clamp member 364 and the connector body 362 so as to maintain the clamp member 364 and the connector body 362 in a desired orientation relative to one another, for example. A first one of the tabs 382 may cooperate with the notch 377 to substantially encircle or otherwise retain a rod portion 258 or a rod portion 280 in the notch 377, while a second one of the two tabs 382 may be compressed against the rod portion 374 when the clamp member 364 is connected to the connector body 362, for example.

To connect the clamp member 364 to the connector body 362, the protrusion 380 may be inserted in the notch 376 so that the openings 368 and 370 are aligned with one another, and the fasteners 366 and the washers 372 may be used to threadingly connect the clamp member 364 to the connector body 362, for example. The tabs 382 and/or the clamp member 364 may compress, clamp, squeeze, or otherwise retain the rod portion 258 or the rod portion 280 into the notch 377, for example. In some exemplary embodiments, the rod portion 258 and/or the rod portion 280 may be maintained in a substantially fixed position inside the notch 376 by the clamp member 364, as will be appreciated by persons of ordinary skill in the art. The fasteners 366 may be staked once they are secured in the openings 368 and 370, in some exemplary embodiments, so as to substantially prevent the fasteners 366 from backing out during use of the connector 360.

The connector 360 may function to allow adjustability in the length of a bone support apparatus 100 according to the inventive concepts disclosed herein, for example, by connecting to a rod portion 258 or 280 and to an ilium connector 300, or to any other desired ilium or rib connector disclosed herein, for example, so that the length of the bone support apparatus 100 may be adjusted by sliding the rod portion 258 and/or 280 relative to the connector 360, and securing the desired length by securely tightening the one or more fasteners 366 of the connector 360, for example. Such adjustability may be used to adjust the bone support apparatus 100 during the initial insertion procedure, after which the connector 360 may not be further adjusted and the length of the bone support apparatus 100 may be adjusted as described above, for example. In some exemplary embodiments, however, the connector 360 may be adjusted in subsequent procedures to provide additional adjustability to the bone support apparatus 100, as will be appreciated by persons of ordinary skill in the art.

Figure 34:
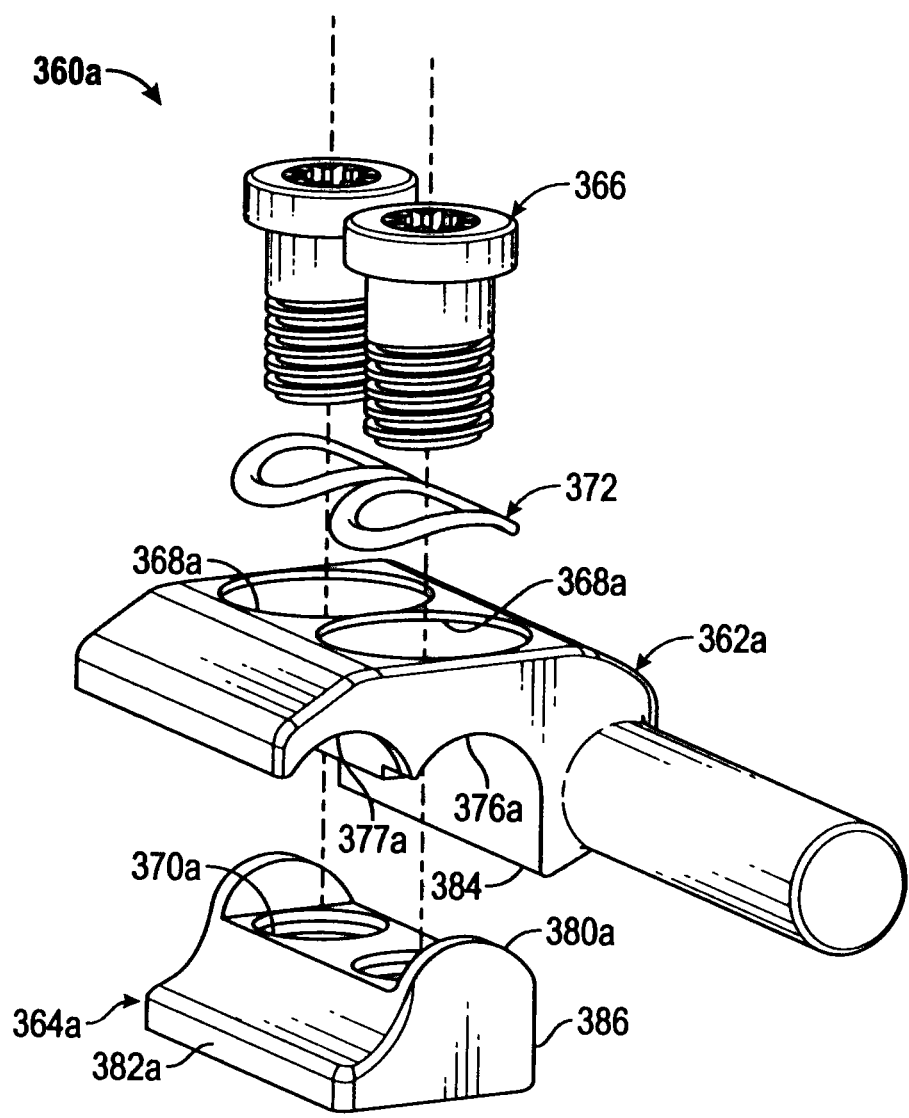
FIG. 34 is an exploded, perspective view of another embodiment of a connector.

Referring now to FIG. 34, shown therein is another embodiment of a connector 360a according to the inventive concepts disclosed herein. The connector 360a may be implemented and function substantially similarly to the connector 360, except that the connector 360a includes a connector body 362a including a side 384, and a clamp member 364a including a protrusion 380a, a tab 382a, and a side 386, for example. The protrusion 380a may be configured to be inserted into a notch 376a so that the side 386 rests against the side 384, and so that the tab 382a cooperates with a notch 377a to partially or substantially encircle a rod portion 258 or 280 as described above, for example. The protrusion 380a and the notch 376a may optionally include any desired corresponding keying features to ensure an optimal fit between the clamp member 364a and the connector body 362a, so as to maintain the clamp member 364a and the connector body 362a in a desired orientation relative to one another, for example.

Further, the side 384 and the side 386 may cooperate with one another to maintain the orientation of the connector body 362a and the clamp member 364a relative to one another.

The clamp member 364a may further include one or more threaded openings 370a intersecting the protrusion 380a and configured to correspond to and align with one or more of the openings 368a when the protrusion 380a is inserted into the notch 376a, for example. In some exemplary embodiments, the clamp member 364 and the clamp member 364a may be interchangeable with one another, as will be appreciated by persons of ordinary skill in the art.

As will be appreciated by persons or ordinary skill in the art having the benefit of the instant disclosure, the connector 360a may function substantially similarly to the connector 360 as described above.

From the above description, it is clear that the inventive concepts disclosed herein are well adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished within the scope of the inventive concepts disclosed and as defined in the appended claims.

What is claimed is:

1. A bone support apparatus, comprising:
   a first bone connector configured to contact a first bone of a patient;
   an ilium connector being a substantially U-shaped clamp structure with a first leg and a second leg, each of the first leg and the second leg having an inward facing surface for contacting the ilium of the patient, each of the inward facing surfaces having a plurality of teeth to bite into opposing sides of the ilium of the patient when the ilium connector is positioned over a crest of the ilium with the first leg positioned on an anterior side of the ilium and the second leg positioned on a posterior side of the ilium; and
   an adjustable rod assembly comprising:
      a first elongated member connected to the first bone connector;
      a second elongated member connected to the ilium connector; and
      an expansion member constructed of a resilient material and having a first end adjustably connected to the first elongated member and a second end adjustably connected to the second elongated member, such that a distance between the first bone connector and the ilium connector is adjustable by moving at least one of the first end of the expansion member relative to the first elongated member and the second end of the expansion member relative to the second elongated member.

2. The apparatus of claim 1, wherein the resilient material has a tensile modulus substantially similar to human cortical bone.

3. A bone support kit, comprising:
   a first bone connector configured to contact a first bone of a patient;
   an ilium connector being a substantially U-shaped clamp structure with a first leg and a second leg, each of the first leg and the second leg having an inward facing surface for contacting the ilium of the patient, each of the inward facing surfaces having a plurality of teeth to bite into opposing sides of the ilium of the patient when the ilium connector is positioned over a crest of the ilium with the first leg positioned on an anterior side of the ilium and the second leg positioned on a posterior side of the ilium; and an adjustable rod assembly configured to be connected to the first bone connector and the ilium connector, the adjustable rod assembly comprising:

a first elongated member configured to connect to the first bone connector;

a second elongated member configured to connect to the ilium connector; and an expansion member constructed of a resilient material and having a first end adjustably connectable to the first elongated member and a second end adjustably connectable to the second elongated member, such that a distance between the first bone connector and the ilium connector is adjustable by moving at least one of the first end of the expansion member relative to the first elongated member and the second end of the expansion member relative to the second elongated member.

4. The kit of claim 3, wherein the resilient material has a tensile modulus substantially similar to human cortical bone.

5. A bone support apparatus, comprising:
a rib connector configured to attach to a rib of a patient;
an ilium connector configured to bite an ilium of the patient; and
an adjustable rod assembly having a first end connected to the rib connector and a second end connected to the ilium connector, the adjustable rod assembly configured to adjust a distance between the first end and the second end, wherein the ilium connector comprises:
a base connected to the second end of the adjustable rod assembly;
an ilium cradle
being a substantially U-shaped clamp structure connected to the base and having a first leg and a second leg, each of the first leg and the second leg having an inward facing surface for contacting the ilium of the patient, each of the inward facing surfaces having a plurality of teeth to bite into opposing sides of the ilium of the patient when the ilium connector is positioned over a crest of the ilium with the first leg positioned on an anterior side of the ilium and the second leg positioned on a posterior side of the ilium.

6. The bone support apparatus of claim 5, wherein the the teeth of the first leg and the second leg are unidirectional and extend in a direction away from a distal end of the first leg and the second leg.

7. The bone support apparatus of claim 6, wherein the ilium cradle has a resilient attachment end connecting the first leg and the second leg allowing the first leg and the second leg to splay.

* * * * *